United States Patent [19]
Pugin

[11] Patent Number: 5,627,293
[45] Date of Patent: May 6, 1997

[54] SILYLATED FERROCENYLDIPHOSPHINES, SILYLATED FERROCENYLDIPHOSPHINES BOUND TO INORGANIC OR POLYMERIC ORGANIC SUPPORTS AND ALSO METAL COMPLEXES THEREOF, THEIR PREPARATION AND USE

[75] Inventor: Benoit Pugin, Münchenstein, Switzerland

[73] Assignee: Ciba-Geigy Corporation, Tarrytown, N.Y.

[21] Appl. No.: 606,156

[22] Filed: Feb. 23, 1996

[30] Foreign Application Priority Data

Feb. 24, 1995 [CH] Switzerland .............................. 543/95

[51] Int. Cl.$^6$ .............................................. C07F 7/08
[52] U.S. Cl. .......................... 556/11; 585/277; 564/375; 564/415; 564/422; 564/423; 526/347.2; 502/153; 502/155; 502/158
[58] Field of Search .............................. 556/11; 585/285, 585/277; 564/375, 415, 422, 423; 526/347.2; 502/153, 155, 158

[56] References Cited

U.S. PATENT DOCUMENTS

| | | |
|---|---|---|
| 3,759,967 | 9/1973 | Sollott et al. .............................. 556/11 |
| 4,994,615 | 2/1991 | Spindler et al. ........................... 564/304 |
| 5,306,853 | 4/1994 | Pugin et al. ............................... 585/269 |
| 5,371,256 | 12/1994 | Togni et al. ............................... 556/11 X |
| 5,416,228 | 5/1995 | Ewen et al. ............................... 556/11 X |
| 5,432,289 | 7/1995 | Pugin et al. ............................... 549/221 |
| 5,466,844 | 11/1995 | Spindler et al. ........................... 556/11 |

FOREIGN PATENT DOCUMENTS

96/16971  6/1996  WIPO .

OTHER PUBLICATIONS

Tae–Jeong Kim et al., Bul. Kar. Chem. Soc. 13, pp. 588–592 (1992).
K. Achiwa, J. Chem. Japan, Soc., Chemistry Letters, pp. 905–908 (1978).
W. R. Cullen, J. of Organomet Chem. 333 (1987) pp. 269–280.
J. Mol. Catal., 51, (1989), 13–27, Van den Berg et al.
J. M. Frechet et al., Polymer, 20 (1979) 675–680.

Primary Examiner—Paul F. Shaver
Attorney, Agent, or Firm—Kevin Mansfield; William A. Teoli, Jr.

[57] ABSTRACT

The invention relates to ferrocenyldiphosphine ligands containing a silylene group, ferrocenyldiphosphines bound to inorganic or polymeric organic supports by this silylene group, their preparation and also their metal complexes with transition metals such as rhodium or iridium. The invention also relates to the use of these complexes for hydrogenating organic double or triple bonds, in particular olefinic double bonds and carbon-heteroatom double bonds. The complexes are particularly suitable for enantioselective hydrogenation using chiral diphosphines and prochiral unsaturated compounds.

The preparation of these immobilized ferrocenyldiphosphines has only been made possible by the provision of correspondingly functionalized ferrocenyldiphosphines. These compounds and their preparation are likewise novel.

Accordingly, the invention also provides compounds of the formula I

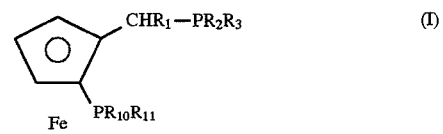

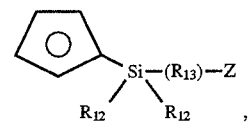

(I)

in which $R_1$ is $C_1$–$C_8$alkyl, phenyl or phenyl substituted by from 1 to 3 $C_1$–$C_4$alkyl or $C_1$–$C_4$alkoxyalkoxy groups;

$R_2$, $R_3$, $R_{10}$ and $R_{11}$ are, independently of one another, $C_1$–$C_{12}$alkyl, $C_5$–$C_{12}$cycloalkyl, phenyl, $C_5$–$C_{12}$cycloalkyl substituted by $C_1$–$C_4$alkyl or $C_1$–$C_4$alkoxy, or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —[+$NR_7R_8R_9$]$X^-$ or $C_1$–$C_5$fluoroalkyl groups; or the groups —$PR_2R_3$ and —$PR_{10}R_{11}$ are each, independently of one another, a radical of the formula II, IIa, IIb or IIc

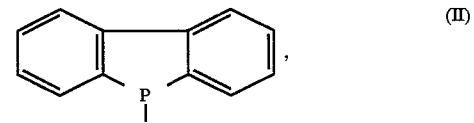

(II)

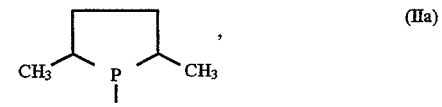

(IIa)

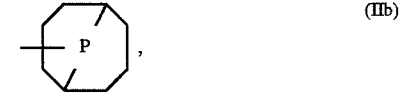

(IIb)

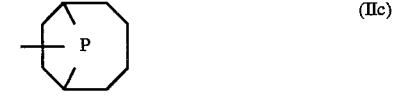

(IIc)

and $R_4$, $R_5$ and $R_6$ are, independently of one another, $C_1$–$C_{12}$alkyl or phenyl;

$R_7$ and $R_8$ are H, $C_1$–$C_{12}$alkyl, phenyl or $R_7$ and $R_8$ are together tetramethylene, pentamethylene or 3-oxa-1,5-pentylene, $R_9$ is H or $C_1$–$C_4$alkyl;

$R_{12}$ are identical or different radicals and are, independently of one another, $C_1$–$C_{12}$alkyl, $C_3$–$C_7$cycloalkyl, benzyl or phenyl or together are $C_5$–$C_{12}$alkylene and $R_{13}$ is $C_1$–$C_{12}$alkylene or phenylene, M is H or an alkali metal, $X^-$ is the anion of a monobasic acid, Z is Cl, $NH_2$, NH—$C_1$—$C_{12}$alkyl, or a group —A—CO—NH—$R_{14}$—Si($R_a$)$_n$(OR$_{15}$)$_{3-n}$, in which A is NH or N($C_1$–$C_{12}$alkyl), $R_{14}$ is $C_1$–$C_{12}$alkylene, $R_{15}$ is $C_1$–$C_{12}$alkyl, $R_a$ is $C_1$–$C_4$alkyl or OR$_{15}$, n is 0, 1 or 2;

where the compounds of the formula I are present in the form of their racemates and diastereomers or mixtures of diastereomers.

26 Claims, No Drawings

SILYLATED FERROCENYLDIPHOSPHINES, SILYLATED FERROCENYLDIPHOSPHINES BOUND TO INORGANIC OR POLYMERIC ORGANIC SUPPORTS AND ALSO METAL COMPLEXES THEREOF, THEIR PREPARATION AND USE

The invention relates to ferrocenyldiphosphine ligands containing a silylene group, ferrocenyldiphosphines bound to inorganic or polymeric organic supports by this silylene group, their preparation and also their metal complexes with transition metals such as rhodium or iridium. The invention also relates to the use of these complexes for hydrogenating organic double or triple bonds, in particular olefinic double bonds and carbon-heteroatom double bonds. The complexes are particularly suitable for enantioselective hydrogenation using chiral diphosphines and prochiral unsaturated compounds.

EP-A-0 256 982 describes the enantioselective hydrogenation of ketimines to optically active secondary amines with the aid of chiral dioxolane-iridiumdiphosphine complexes as homogeneous catalysts. However, the expensive catalysts cannot be recovered, or can be recovered only by means of complicated separation methods, which is always associated with undesired losses. Furthermore, these catalysts have a high loss in activity during use, so that reuse of the recovered homogeneous catalysts is impossible and/or uneconomical. There is therefore a need for catalysts which can be easily separated off and reused, and whose activity and particularly selectivity are largely retained on repeated use.

EP-A-0 496 699 and EP-A-0 496 700 describe dioxolane- and pyrrolidine-diphosphines containing silane groups and also their rhodium or iridium complexes which are fixed to an inorganic support material, for example silicates. In this way, hydrogenation gives a heterogeneous reaction mixture from which the inorganically fixed catalyst can easily be separated after the reaction has ended.

Other supports which have become known are polymeric support materials in which the diphosphine component is located on a copolymerizable building block which is then copolymerized together with other monomers so that the diphosphine or its metal complex is bound directly into the polymer chain.

In J. Chem. Japan Soc., Chemistry Letters, pages 905 to 908 (1978), K. Achiwa describes polystyrene copolymers whose benzene radicals contain pyrrolidine-diphosphine-N-carbonyl groups complexed with rhodium. The synthesis of the monomers is difficult and the hydrogenation of prochiral olefins using these heterogeneous catalysts is, compared with catalysts not bound to a polymer, associated with lowering of the activity, the productivity and the enantioselectivity. The pyrrolidine-diphosphine ligands are fixed via a para-amide bond directly to the benzene radical of the styrene which forms one part of the copolymer while the other part of the copolymer framework is formed by hydroxyethyl methacrylate. This direct bonding to the basic polymer framework severely restricts the freedom of movement of the diphosphine ligands, which can have an adverse effect on the catalytic properties.

A further disadvantage of this fixing concept is that the polymer has to be built up from the start, which is complicated and leads to imprecisely forseeable properties in respect of solubility in organic solvents, separability or precipitability after the hydrogenation reaction. Such a polymer structure favours the partial inclusion of the catalytically active part and thus leads to further reduced activity and productivity.

In J. of Organometallic Chemistry, 333 (1987), 269–280, W. R. Cullen et. al. describe ferrocene derivates such as N, N-dimethyl-1-(2-diphenylphosphinoferrocenyl)ethylamine which is directly bound to an oxidized polystyrene group. In the procedure proposed there, at most 20% of the ferrocene derivative used is bound to the polymeric support and the ferrocenyl ligand is unspecifically and unselectively partially bound to the polymer via one or other cyclopentadienyl ring. The direct bonding to the polymer framework likewise restricts the freedom of movement of the phosphine ligands.

On the other hand, organic polymeric materials can have larger amounts of the catalytically active compounds fixed to them than can inorganic supports, which means that less catalyst composition has to be used for the hydrogenation reaction.

In view of this, it seems desirable to start from support materials having known properties and to modify these with catalytically active compounds in such a way that the properties are only slightly altered and no inclusions or other changes occur on the catalytically active part. Here, depending on the hydrogenation reaction, inorganically or organically bound ferrocenyldiphosphine ligands can be more advantageous.

The reaction to be catalysed can, for the example of ferrocenyldiphosphine ligands bound to a polymer, be carried out heterogeneously or homogeneously depending on the choice of polymer. The polymer can be selected and also subsequently modified in a targeted manner so that, after the reaction, the catalyst can easily be separated off and reused. The catalysts can be reused a plurality of times. The choice of the polymer enables the catalyst to be optimally matched to the reaction medium during the hydrogenation step and then to be completely separated off, which is particularly important for hydrogenations carried out on a large scale.

In all cases, the recovery of the noble metals present is made easier when the catalyst has to be replaced after a great deal of recycling.

It has now been found that ferrocenyldiphosphines containing an organic radical bound to a cyclopentadienyl ring via a silylene group give functionalized ferrocenyldiphosphine ligands which can be immobilized on either inorganic or polymeric organic support materials. The immobilized ferrocenyldiphosphine ligands form rhodium and iridium complexes which can be used as highly effective catalysts in enantioselective hydrogenations of carbon-carbon, carbon-nitrogen or carbon-oxygen double bonds. The selectivity and the total yield are surprisingly high for immobilized systems. The iridium catalysts are very well suited, in particular, for imine hydrogenation, since they have the cleary highest activity, selectivity and the highest catalyst productivity compared with other immobilized systems. The catalysts can easily be separated from the reaction solution and reused. Virtually no metal losses occur. For this reason, large-scale hydrogenations in particular can be economically carried out using these immobilized catalysts.

The preparation of these immobilized ferrocenyldiphosphines has only been made possible by the provision of correspondingly functionalized ferrocenyldiphosphines. These compounds and their preparation are likewise novel.

The invention accordingly provides compounds of the formula I

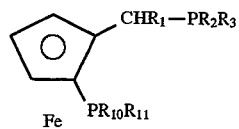

(I)

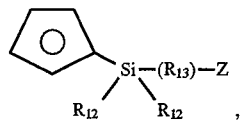

in which $R_1$ is $C_1$–$C_8$alkyl, phenyl or phenyl substituted by from 1 to 3 $C_1$–$C_4$alkyl or $C_1$–$C_4$alkoxy groups;

$R_2$, $R_3$, $R_{10}$ and $R_{11}$, are independently of one another, $C_1$–$C_{12}$alkyl, $C_5$–$C_{12}$cycloalkyl, phenyl, $C_5$–$C_{12}$cycloalkyl substituted by $C_1$–$C_4$alkyl or $C_1$–$C_4$alkoxy, or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —[$^+NR_7R_8R_9$] $X^-$ or $C_1$–$C_5$fluoroalkyl groups; or the groups —$PR_2R_3$ and —$PR_{10}R_{11}$ are each, independently of one another, a radical of the formula II, IIa, IIb or IIc

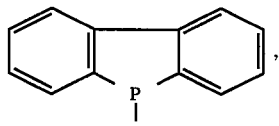

(II)

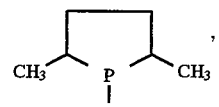

(IIa)

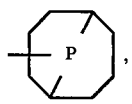

(IIb)

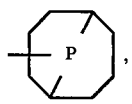

(IIc)

and $R_4$, $R_5$ and $R_6$ are, independently of one another, $C_1$–$C_{12}$alkyl or phenyl;

$R_7$ and $R_8$ are H, $C_1$–$C_{12}$alkyl, phenyl or $R_7$ and $R_8$ are together tetramethylene, pentamethylene or 3-oxa-1,5-pentylene, $R_9$ is H or $C_1$–$C_4$alkyl;

$R_{12}$ are identical or different radicals and are, independently of one another, $C_1$–$C_{12}$alkyl, $C_3$–$C_7$cycloalkyl, benzyl or phenyl or together are $C_5$–$C_{12}$alkylene and $R_{13}$ is $C_1$–$C_{12}$alkylene or phenylene, M is H or an alkali metal, $X^-$ is the anion of a monobasic acid, Z is Cl, $NH_2$, NH—$C_1$–$C_{12}$alkyl, or a group—A—CO—NH—$R_{14}$—Si($R_a$)$_n$(O$R_{15}$)$_{3-n}$, in which A is NH or N($C_1$–$C_{12}$alkyl), $R_{14}$ is $C_1$–$C_{12}$alkylene, $R_{15}$ is $C_1$–$C_{12}$alkyl, $R_a$ is $C_1$–$C_4$alkyl or O$R_{15}$, n is 0, 1 or 2;

and the compounds of the formula I are present in the form of their racemates and diastereomers or mixtures of diastereomers.

An alkyl group $R_1$ is preferably linear. It preferably contains from 1 to 4 C atoms. Examples of such an alkyl group are methyl, ethyl, n- and i-propyl, n-, i- and t-butyl, pentyl, hexyl, heptyl and octyl. Preference is given to methyl and ethyl and particular preference is given to methyl.

A substituted phenyl group preferably contains 1 or 2 substituents. Examples of alkyl substituents are methyl, ethyl, n- and i-propyl, n-, i- and t-butyl; preference is given to methyl and ethyl. Examples of alkoxy substituents are methoxy, ethoxy, n- and i-propoxy, n-, i- and t-butoxy; preference is given to methoxy and ethoxy. In a group of compounds of the formula I, R1 is preferably phenyl or phenyl substituted by 1 or 2 $C_1$–$C_4$alkyl or $C_1$–$C_4$alkoxy groups.

Alkyl groups $R_2$, $R_3$, $R_{10}$ and $R_{11}$ can be linear or branched and they preferably contain from 1 to 8, particularly preferably from 1 to 4, C atoms. Examples of such an alkyl group are methyl, ethyl, n- and i-propyl, n-, i- and t-butyl, pentyl, hexyl, heptyl, octyl, nonyl, decyl, undecyl and dodecyl. Preference is given to methyl, ethyl, n- and i-propyl, n-, i- and t-butyl. If $R_2$, $R_3$ and/or $R_{10}$ and $R_{11}$ are identical and are alkyl, they are particularly preferably i-propyl or t-butyl.

Cycloalkyl groups $R_2$, $R_3$, $R_{10}$ and $R_{11}$ preferably contain from 5 to 8, particularly preferably 5 or 6, ring C atoms. Examples of cycloalkyl groups are cyclopentyl, cyclohexyl, cycloheptyl, cyclooctyl, cyclodecyl and cyclododecyl. Preference is given to cyclopentyl and cyclohexyl and particular preference is given to cyclohexyl.

The cycloalkyl group can be substituted, for example by from 1 to 3 alkyl- or alkoxy substituents. Examples of such substituents have been given above. Preference is given to methyl and ethyl and to methoxy and ethoxy. Examples of substituted cycloalkyl groups are methylcyclopentyl, methoxycyclopentyl, methylcyclohexyl and methoxycyclohexyl.

$R_2$, $R_3$, $R_{10}$ and $R_{11}$ can be, independently of one another, unsubstituted or substituted phenyl. When they are substituted phenyl, they preferably contain 1, 2 or 3 substituents. If the phenyl contains 2 or 3 substituents, these can be identical or different.

Examples of the substituents alkyl and alkoxy have been given above; preferred alkyl- and alkoxy substituents for phenyl are methyl, ethyl and methoxy and ethoxy.

If the phenyl substituent is halogen, it is preferably —F, —Cl or —Br.

If the phenyl substituent is $C_1$–$C_5$fluoroalkyl, it is completely or partially fluorinated $C_1$–$C_5$alkyl. Examples of such groups are the positional isomers of mono- to decafluoropentyl, mono- to octafluorobutyl, mono- to hexafluoropropyl, mono- to tetrafluoroethyl and also mono- and difluoromethyl. Among these partially fluorinated alkyl radicals, those of the formulae —$CF_2H$ and —$CF_2$($C_1$–$C_4$alkyl) are particularly preferred. Particular preference is given to a perfluorinated alkyl. Examples of such a group are perfluoropentyl, perfluorobutyl, perfluoropropyl, perfluoroethyl and, in particular, trifluoromethyl. The flourine-substitued alkyl groups are preferably bonded in the 3, 4 and 5 positions.

$R_4$, $R_5$ and $R_6$ can be linear or branched alkyl containing preferably from 1 to 8 and particularly preferably from 1 to 4 C atoms. Examples of alkyl groups have been given above. Alkyl is preferably methyl, ethyl, n-propyl, n-butyl und t-butyl. The substituent —$SiR_4R_5R_6$ is particularly preferably trimethylsilyl.

Among the acid phenyl substituents —$SO_3M$, —$CO_2M$ and —$PO_3M$, the group —$SO_3M$ is preferred. M is preferably H, Li, Na and K.

When $R_7$ and $R_8$ are alkyl, they preferably contain from 1 to 6, particularly preferably from 1 to 4, C atoms. The alkyl is preferably linear. Preferred examples are methyl, ethyl, n-propyl and n-Butyl.

When $R_9$ is alkyl, it is preferably methyl.

As the anion of a monobasic acid, $X^-$ is preferably $Cl^-$, $Br^-$ or the anion of a carboxylic acid, for example formate, acetate, trichloroacetate or trifluoroacetate.

Preferred examples of $R_2$, $R_3$, $R_{10}$ and $R_{11}$ as substituted phenyl are 2-methyl-, 3-methyl-, 4-methyl-, 2- or 4-ethyl-, 2- or 4-i-propyl-, 2- or 4-t-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(Dimethylamino), 2- or 4-$SO_3H$-, 2- or 4-$SO_3Na$-, 2- or 4-[$^+NH_3Cl$]-, 3,4,5-trimethylphen-1-yl, 2,4,6-trimethylphen-1-yl, 4-trifluoromethylphenyl or 3,5-di(trifluoromethyl)phenyl.

If $R_2$ and $R_3$ are identical, $R_2$ and $R_3$ are preferably phenyl, cyclohexyl, 2- or 4-methylphen-1-yl, 2- or 4-methoxyphen-1-yl, 2- or 4-(dimethylamino)phen-1-yl, 3,5-dimethyl-4-(dimethyl-amino)phen-1-yl and 3,5-dimethyl-4-methoxyphen-1-yl.

If $R_2$ and $R_3$ are different, $R_2$ is preferably phenyl and $R_3$ is preferably cyclohexyl, 2- or 4-methylphen-1-yl, 2- or 4-methoxyphen-1-yl, 4-(dimethylamino)phen-1-yl, 3,5-dimethyl-4-(dimethylamino)phen-1-yl, 3,5-dimethyl-4-methoxyphen-1-yl or 4-t-butylphen-1-yl.

In a preferred embodiment, $R_2$ and $R_3$ are identical radicals and are cyclohexyl or phenyl.

In a particularly preferred embodiment, in formula I $R_1$ is methyl and $R_2$ and $R_3$ are each cyclohexyl or phenyl.

If $R_{10}$ and $R_{11}$ are identical, $R_{10}$ and $R_{11}$ are preferably cyclohexyl, t-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl, but particularly preferably cyclohexyl, 4-methylphen-1-yl or t-butyl.

If $R_{10}$ and $R_{11}$ are different, $R_{10}$ is preferably phenyl and $R_{11}$ is preferably cyclohexyl, 2- or 4-methylphen-1-yl, 2- or 4-methoxyphen-1-yl, 4-(dimethylamino)phen-1-yl, 3,5-dimethyl-4-(dimethylamino)phen-1-yl, 3,5-dimethyl-4-methoxyphen-1-yl or 4-t-butylphen-1-yl.

In a particularly preferred group of compounds of the formula I, $R_1$ is methyl and $R_2$ and $R_3$ are each cyclohexyl or phenyl and $R_{10}$ and $R_{11}$ are phenyl, cyclohexyl or t-butyl.

$R_{12}$ is preferably $C_1$–$C_4$alkyl, particularly preferably methyl. $R_{13}$ is preferably $C_3$–$C_6$alkylene, particularly preferably propylene.

$R_{14}$ is preferably $C_1$–$C_6$alkylene.

$R_{15}$ is preferably $C_1$–$C_4$alkyl, particularly preferably methyl.

$R_a$ is preferably $OR_{15}$.

The invention also provides a process for preparing compounds of the formula I, wherein, in a first step, a) compounds of the formula III

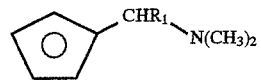
(III)

are lithiated in a known manner with butyllithium in an inert organic solvent in the presence of an amine complexing agent for lithium, the reaction product is subsequently reacted with a mixture of the compounds of the formulae IV ClPR$_{10}$R$_{11}$ (IV) and V ClSi(R$_{12}$)$_2$—(R$_{13}$)—Cl (V) to give compounds of the formula VI

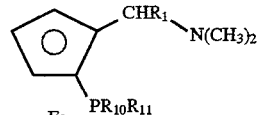
(VI)

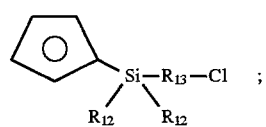

in a second step, b) Compounds of the formula VI are reacted in an organic solvent with compounds of the formula VII HPR$_2$R$_3$ (VII) to give compounds of the formula Ia

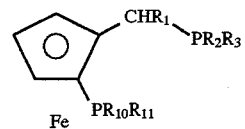
(Ia)

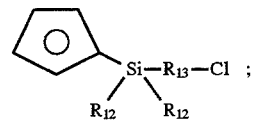

c) Compounds of the formula Ia are reacted with compounds of the formula VIII NH$_2$(C$_1$–C$_2$alkyl) (VIII) to give compounds of the formula Ib

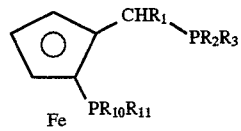
(Ib)

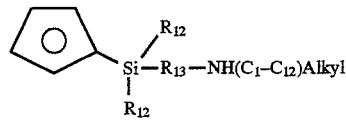

or compounds of the formula Ia are reacted first with potassium phthalimide and subsequently with hydrazine to give compounds of the formula Ic

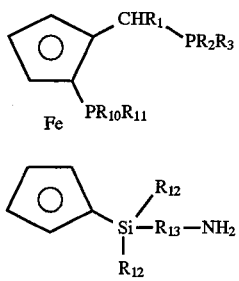

(Ic)

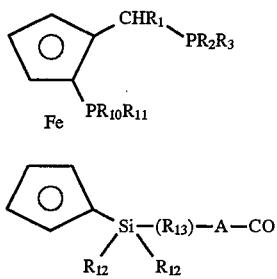

and, if desired in a further step, d) Compounds of the formula Ib or Ic are reacted with a compound of the formula IX $(R_a)_n(R_{15}O)_{3-n}Si-R_{14}-NCO$ (IX) to give compounds of the formula Id

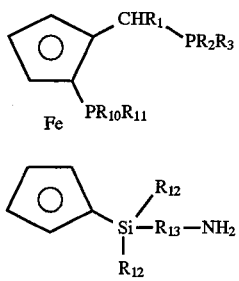

(Id)

$$\underset{R_{12}}{\overset{\phantom{x}}{\diagdown}}Si-(R_{13})-A-CO-NH-R_{14}-Si(OR_{15})_{3-n}(R_a)_n,$$

in which the radicals $R_a$, $R_1$, $R_2$, $R_3$, $R_{10}$, $R_{11}$, $R_{12}$, $R_{13}$, $R_{14}$, $R_{15}$, A and n are as defined above, including the preferred embodiments.

An example of an amine complexing agent for Li is N,N,N,N-tetramethylethylenediamine.

The compounds of the formulae III, IV, V, VII, VIII and IX are known and some are commercially available. They can otherwise be prepared by the methods described in the lierature.

The compounds of the formulae VI, Ia, Ib, Ic and Id are novel, subject-matter of the invention and are encompassed by the formula I. They are important intermediates for ferrocenyldiphosphines able to be immobilized on inorganic or organic polymer support materials, and also their rhodium and iridium complexes.

The process for their preparation is, particularly in the reaction step a), likewise novel and subject-matter of the invention. The reaction steps b), c) and d) are processes by analogy which are described, for example, for b) in EP-A-612 758, and d) in EP-A-496 699. The step c) is known to those skilled in the art from available textbooks on organic chemistry.

The mixture of compounds of the formulae IV and V in the reaction step a) is preferably in a molar ratio of from 1:10 to 10:1, particularly preferably from 1:1 to 10:1.

The reaction step a) is preferably carried out at a temperature of from –40° C. to +70° C.; the mixture of the compounds of the formulae IV and V is particularly preferably added at a temperature of from 0° C. to –40° C., very particularly preferably at a temperature of from 0° C. to –15° C.

The compound of the formula V in the reaction step a) is particularly preferably 1-(dimethylchlorosilyl)-3-chloropropane.

The reaction step b) is described, for example, in EP-A-612 758.

The reaction temperature in step b) can be, for example, from 20° to 150° C., preferably from 40° to 100° C. Suitable solvents are polar protic and aprotic solvents which can be used alone or as a mixture of two or more solvents. Some examples of solvents are alkanols, for example methanol and ethanol, and carboxylic acids, for example formic acid and acetic acid.

The compounds of the formulae Ia to Id are obtained as racemates, pure enantiomers or mixtures of enantiomers. Racemates and mixtures of enantiomers can be separated into the stereoisomers by known methods, with chromatographic methods generally being preferred.

The isolation and purification of the componds of the formula I is carried out by methods known per se, for example distillation, extraction, crystallization and/or chromatographic methods.

In a preferred embodiment, hydrazine is used in the reaction step c) in the form of hydrazine hydrate.

Further details of the process conditions are given in the examples.

The invention further provides metal complexes of the formula Xa or Xb of rhodium or iridium with the compounds of the formula I

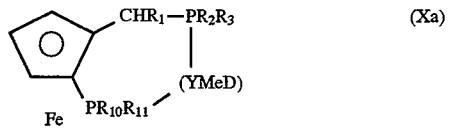

(Xa)

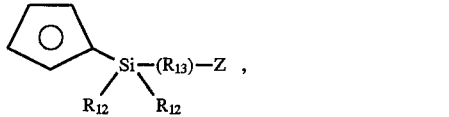

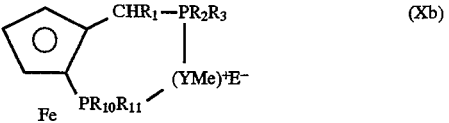

(Xb)

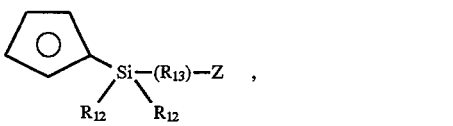

in which $R_1$, $R_2$, $R_3$, $R_{10}$, $R_{11}$, $R_{12}$ $R_{13}$ and Z are as defined and preferred above;

Y is two monoolefin ligands or a diene ligand;

Me is Ir or Rh;

D is —Cl, —Br, —I;

$E^-$ is the anion of an oxygen acid or a complex acid.

Preference is given to metal complexes in which Y is 1,5-hexadiene, 1,5-cyclooctadiene or norbornadiene.

In the metal complexes of the invention, D is preferably —Cl or —Br.

In the preferred metal complexes, $E^-$ is $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

The invention further provides a process for preparing metal complexes, wherein compounds of the formula I are reacted with a metal compound of the formula $[Me(Y)D]_2$ or $Me(Y)_2^+E^-$ in which Me is rhodium or iridium and Y, D and $E^-$ are as defined and preferred above.

The reaction is advantageously carried out in a inert gas atmosphere, for example argon, and conveniently at temperatures of from 0° to 40° C., preferably at room temperature. Preference is given to using a solvent or mixture of solvents, for example hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, ethylene glycol dimethyl ether) or mixtures thereof.

The compounds of the formulae Xa and Xb are in themselves homogeneous catalysts which can be used for hydrogenations of unsaturated organic compounds.

The invention further provides inorganic or organic polymeric support materials to which ferrocenyldiphosphines are bound, wherein the 1 and 2 positions of the one cyclopentadienyl ring bears tertiary phosphine groups of which one is bound directly and the other via a group $CHR_1$ to the cyclopentadienyl ring and the other cyclopentadienyl radical bears a silylene group —$Si(R_{12})_2$—$R_{13}$—A— which is bound via the Si atom and forms one end of an organic bridge at the other end of which the inorganic or polymeric organic support is bound via the group A directly or via an additional further group, where the radicals A, $R_{12}$ and $R_{13}$ are as defined and preferred above.

The invention also provides a process for preparing the support materials of the invention, wherein a ferrocenyldiphosphine in which the 1 and 2 positions of the one cyclopentadienyl ring bear tertiary phosphine groups of which one is bound directly and the other via a group $CHR_1$ to the cyclopentadienyl ring and the other cyclopentadienyl radical bears a silylene group —$Si(R_{12})_2$—$R_{13}$—A— bound via the Si atom is reacted via the —$Si(R_{12})_2$—$R_{13}$—A— group a) directly with the groups forming a covalent bond of an inorganic or polymeric organic support material; or b) the group —$Si(R_{12})_2$—$R_{13}$—A— is first reacted with a difunctional bridging group and this is then reacted with the groups forming a covalent bond of an inorganic or polymeric organic support material.

The term tertiary phosphine group refers to a phosphorus atom bound to 3 carbon atoms as defined, for example, in H. Beyer, Lehrbuch der organischen Chemie, S. Hirzel Vedag Leipzig, Ausgabe 1968 auf Seite 138 definiert ist.

A preferred group comprises a polymeric organic material having structural repeating units of the formula XI

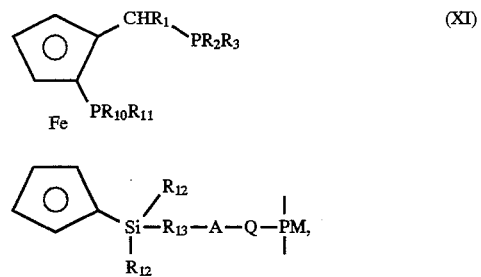

in which A, $R_1$, $R_2$, $R_3$, $R_{10}$, $R_{11}$, $R_{12}$ and $R_{13}$ are as defined above;

Q is a bridging group formed by a diisocyanate;

PM is the radical of a polymer-forming monomer which bears, directly or in a side chain, a hydroxyl group or a primary or secondary amino group as functional group which is bound to the diphosphine via a bridging group Q formed by a diisocyanate.

The diphosphine radicals of the formula I can be present as mixtures of enantiomers, preference being given to polymers containing radicals of the formulae I in the form of the optically active R, R, S,S, R,S oder S,R isomers, based on the position of the phosphine groups.

The choice of the diisocyanate for forming the bridging group Q is not critical per se. In particular, the bridging group Q can be formed by at least 2 C atoms. Suitable diisocyanates which are available on a large scale are described, for example, in Houben Weyl, Makromolekulare Stoffe, Volume E 20, pages 1587 to 1583, 1987 edition.

Preference is given to diisocyanates whose bridging group Q is formed by a linear or branched $C_2$–$C_{20}$alkyl which may be unsubstituted or mono- or polysubstituted by $C_1$–$C_6$-alkyl, $C_1$–$C_6$alkoxy; $C_3$–$C_8$cycloalkyl or heterocycloalkyl which may be unsubstituted or mono- or polysubstituted by $C_1$–$C_6$alkyl, $C_1$–$C_6$alkoxy; linear or branched $C_2$–$C_{20}$alkyl which may be unsubstituted or substituted by $C_1$–$C_6$alkyl, $C_1$–$C_6$alkoxy and is interrupted by $C_3$–$C_8$cycloalkyl or heterocycloalkyl which may be unsubstituted or substituted by $C_1$–$C_6$alkyl, $C_1$–$C_6$alkoxy; phenyl, naphthyl, biphenyl or $C_3$–$C_{10}$heteroaryl which may each be unsubstituted or mono- or polysubstituted by $C_1$–$C_6$alkyl, $C_1$–$C_6$alkoxy; linear or branched $C_2$–$C_{20}$alkyl which may be unsubstituted or substituted by $C_1$–$C_6$alkyl, $C_1$–$C_6$alkoxy and is interrupted by phenyl, naphthyl or $C_3$–$C_{10}$heteroaryl.

Heterocycloalkyl is, for example, pyrrolidine, piperidine, morpholine, oxazolidine, dioxolane or an isocyanuric triester group.

Heteroaryl is, for example, pyridine, pyrimidine, pyrrole, furan, imidazole, pyrazole or triazine.

Particularly preferred diisocyanates are 1,6-bis (isocyanato)hexane, 5-isocyanato-3-(isocyanatomethyl)-1, 1,3-trimethylcyclohexane, 1,3-bis(5-isocyanato-1,3,3-trimethylphenyl)-2,4-dioxo-1,3-diazetidine, 3,6-bis(9-isocyanatononyl)-4,5-di(1-heptenyl)cyclohexene, bis(4-isocyanatocyclohexyl)methane, trans-1,4-bis(isocyanato) cyclohexane, 1,3-bis-(isocyanatomethyl)benzene, 1,3-bis(1-isocyanato-1-methylethyl)benzene, 1,4-bis (2isocyanatoethyl)cyclohexane, 1,3-bis(isocyanatomethyl) cyclohexane, 1,4-bis(1-isocyanato-1-methylethyl)benzene, bis(isocyanato)isododecylbenzene, 1,4-bis(isocyanato) benzene, 2,4-bis(isocyanato)toluene, 2,6-bis(isocyanato) toluene, 2,4-/2,6-bis(isocyanato)toluene, 2-ethyl-1,2,3-tris (3-isocyanato-4-methylanilinocarbonyloxy)propane, N,N'-bis(3-isocyanato-4-methylphenyl)urea, 1,4-bis(3-isocyanato-4-methylphenyl)-2,4-dioxo-1,3-diazetidine, 1,3, 5-tris(3-isocyanato-4-methylphenyl)-2,4,6-trioxohexahydro-1,3,5-triazine, 1,3-bis(3-isocyanato-4-methylphenyl)-2,4,5-trioxoimidazolidine, bis(2-isocyanatophenyl)methane, (2-isocyanatophenyl)(4-isocyanatophenyl)methane, bis(4-isocyanatophenyl) methane, 2,4-bis(4-isocyanatobenzyl)-1-isocyanatobenzene, [4-isocyanato-3-(4-isocyanatobenzyl)phenyl][2-isocyanato-5-(4-isocyanatobenzyl)phenyl]methane, tris(4-isocyanatophenyl)methane, 1,5-bis(isocyanato)naphthalene, or 4,4'-bis(isocyanato)-3,3'-dimethylbiphenyl.

Very particularly preferred diisocyanates are 1,6-bis (isocyanato)hexane, 5-isocyanato-3-(isocyanatomethyl)-1, 1,3-trimethylcyclohexane, 2,4-bis(isocyanato)toluene, 2,6-bis(isocyanato)toluene, 2,4-/2,6-bis(isocyanato)toluene or bis(4-isocyanatophenyl)methane.

The polymers of the invention can be uncrosslinked thermoplastic, crosslinked or structurally crosslinked polymers.

The polymers can be polymers of olefinically unsaturated monomers, for example polyolefins, polyacrylates, polyisoprenes, polybutadiene, polystyrene, polyphenylene, polyvinyl chloride, polyvinylidene chloride or polyallyl compounds. They can also be polyaddition compounds such as polyurethanes or polyethers. Examples of polycondensation products are polyesters or polyamides.

If the polymers are essentially uncrosslinked (thermoplastics), they can be soluble in organic solvents. Partially crosslinked polymers are usually only swellable in organic solvents and highly crosslinked polymers can be insoluble and advantageously porous materials.

Crosslinked polymers (thermosets) can be phenol-aldehyde resins, for example in the form of commercial Bakelites®, urea-formaldehyde or melamine-formaldehyde resins, crosslinked polyurethanes or crosslinked epoxy resins. Suitable crosslinking components for epoxy resins are, in particular, diamines or triamines. Crosslinked polymers based on triglycidyl isocyanurate are also possible.

Other suitable crosslinkers are, for example, unsaturated polyester resins derived from copolyesters of saturated and unsaturated dicarboxylic acids with polyhydric alcohols, and also vinyl compounds.

Likewise possible are crosslinkable acrylic resins derived from substituted acrylic esters, for example from epoxy acrylates, urethane acrylates or polyester acrylates.

A further group is formed by the alkyd resins, polyester resins and acrylate resins which are crosslinked with melamine resins, urea resins, polyisocyanates or epoxy resins.

Among the crosslinked systems, those comprising olefinically unsaturated monomers are preferred, examples being polyacrylates, polyolefins or polystyrene. The crosslinking component is likewise olefinically unsaturated. An example is polystyrene crosslinked with divinylbenzene.

Examples of linear polymers soluble in organic solvents are given below.

The polymers to be used according to the invention are known per se, some of them are commercially available or they can be prepared using known polymerization processes or by subsequent modification of polymers.

The hydroxyl-functional or primary or secondary amino-functional monomers preferably make up from 1 to 100 mol %, particularly preferably from 5 to 100 mol % and very particularly preferably from 10 to 100 mol % of the polymer if this is a soluble or swellable polymer in which the functional group is already present.

If the polymers are crosslinked polymers which are subsequently functionalized, they preferably contain from 1 to 50 mol %, particularly preferably 1–20 mol %, of hydroxyl-functional or primary or secondary amino-functional groups, where the mol % figures are based on the monomer making up most of the polymer.

According to the invention, the loading of the polymer with ferrocenyldiphosphines is preferably between 1 and 100 mol %, particularly preferably between 5 and 50 mol %, based on the available hydroxyl groups or primary or secondary amino groups of the polymer.

The monomers forming the polymer are preferably selected from the group consisting of sytrene, p-methylstyrene or α-methylstyrene, of which at least one contains a bonded hydroxyl group or a bonded primary or secondary amino group as functional group.

Further comonomers which form copolymers with styrene derivatives can be present, for example styrene, p-methylstyrene or α-methylstyrene, butadiene, maleic anhydride, acrylates or methacrylates, as well as ethylene, propylene or butylene. This gives copolymers of, for example, styrene-butadiene, styrene-acrylonitrile, styrene-alkyl methacrylate, styrene-butadiene-alkyl acrylate and methacrylate, styrene-maleic anhdyride, styrene-acrylonitrile-methyl acrylate; mixtures of styrene copolymers and another polymer, for example a polyacrylate, a diene polymer or an ethylene-propylene-diene terpolymer; and also block copolymers of styrene, for example styrene-butadiene-styrene, styrene-isoprene-styrene, styrene-ethylene/butylene-styrene or styrene-ethylene/propylene-styrene.

Likewise suitable are graft copolymers of styrene or α-methylstyrene, for example styrene on polybutadiene, styrene on polybutadiene-styrene copolymers or polybutadiene-acrylonitrile copolymers, styrene and acrylonitrile (or methacrylonitdle) on polybutadiene; styrene, acrylonitrile and methyl methacrylate on polybutadiene; styrene and maleic anhydride on polybutadiene; styrene, acrylonitrile and maleic anhdyride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on poly(alkyl acrylates) or poly(alkyl methacrylates), styrene and acrylonitrile on acrylate-butadiene copolymers.

Preferred comonomers are dienes or acrylic derivatives, for example butadiene, acrylonitdle, alkyl methacrylate, butadiene-alkyl acrylate and methacrylate, maleic anhdyride, acrylonitrile-methyl acrylate, which form random or block copolymers.

Another preferred group of polymers is formed from monomers derived from α,β-unsaturated acids, their esters or amides, whose structural elements contain a bonded hydroxyl group or a bonded primary or secondary amino group as functional group.

Particular preference is give to the monomers from the group of acrylates and their $C_1$–$C_4$alkyl esters, methacrylates and their $C_1$–$C_4$alkyl esters, acrylamide and acrylonitrile whose structural elements contain a bonded hydroxyl group or a bonded primary or secondary amino group as functional group in the ester or amide group.

It is also possible for further copolymer-forming comonomers which are dedved from olefinically unsaturated monomers and form random polymers or block copolymers to be present. Suitable comonomers are acrylates and their $C_1$–$C_4$alkyl esters, methacrylates and their $C_1$–$C_4$alkyl esters, acrylamide and acrylonitrile, and also butadiene, vinyl chloride or vinyl fluoride.

A further group of preferred polymers are formed from monomers containing vinyl alcohol as homopolymer or vinyl alcohol as copolymer with vinyl acetate, stearate, benzoate, maleate, vinyl butyral, allyl phthalate, allylmelamine.

Other preferred polymers are formed from phenol and a $C_1$–$C_4$aldehyde, particularly preferably from phenol and formaldehyde. The polymers are known in the form of phenolformaldehyde resins, in particular as novolaks, and are commercially available.

Another preferred group of polymers is derived from bisglycidyl ethers and diols. These are hydroxyl-functional polyethers which are prepared, for example, from bisglycidyl ethers and bisphenol A.

The polyepoxides can be made up of diepoxide comonomers having preferably from 6 to 40 and particularly preferably from 8 to 30 C atoms and diols as comonomers having preferably from 2 to 200 and particularly preferably from 2 to 50 C atoms. A preferred group derived therefrom is formed from monomers which build up a polymer from cyclic $C_3$–$C_6$ethers or $C_2$–$C_6$alkylene glycols and bisglycidyl ethers. The bisglycidyl ethers can be aromatic, aliphatic or cycloaliphatic.

Further preferred polymers containing hydroxyl groups as functional groups are polysaccharides.

Particular preference is given to partial cellulose acetates, propionates or butyrates, partial cellulose ethers, starch, chitin and chitosan.

Further polymers are derived from polymers containing reducible groups, for example nitrile groups, ketone groups, carboxylic esters and carboxamides.

The reaction medium may also include insoluble polymers which are functionalized on the surface with hydroxyl or amino groups by means of a chemical or physical process. For example, partially unsaturated polymers can be provided on the surface with hydroxyl groups by oxidation, e.g. using hydrogen peroxide. Another possibility is plasma treatment in, for example, an oxygen, nitrogen or ammonia atmosphere. The polymers are preferably in the form of powder. Among these support materials, particular preference is given to polystyrene which has subsequently been functionalized with hydroxyl, amino or hydroxymethyl groups by known methods.

Particularly preferred polymers are those having structural repeating units of at least one monomer of a compound of the formula XIa, XIb, XIc or XId

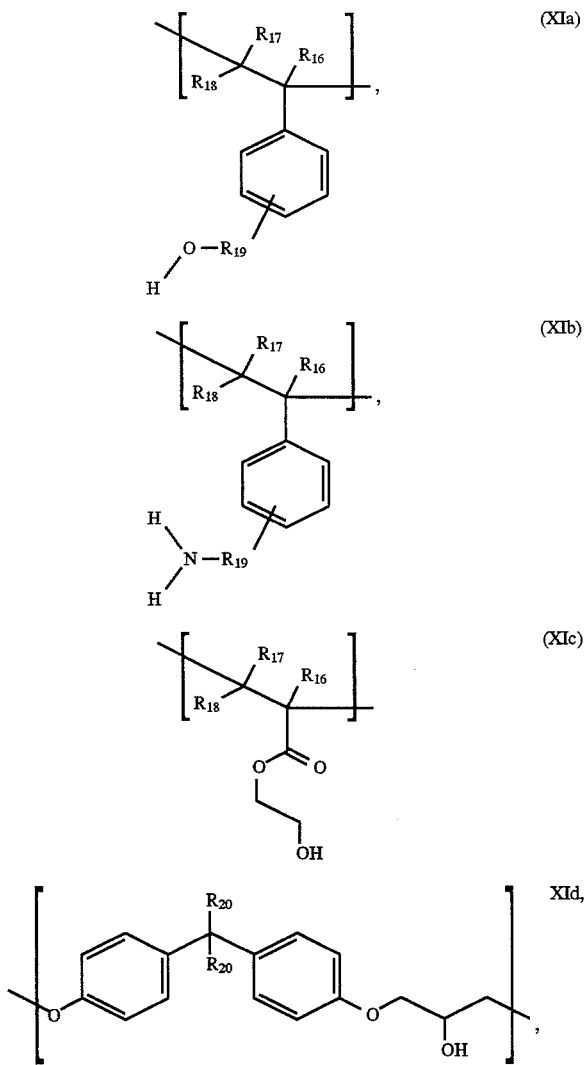

in which $R_{19}$ is $C_1$–$C_4$alkylene and $R_{16}$, $R_{17}$, $R_{18}$ and $R_{20}$ are, independently of one another, hydrogen or $C_1$–$C_4$alkyl. The polymeric organic materials preferably have a molecular weight of from 5000 to 5,000,000 dalton, particularly preferably from 50,000 to 1,000,000 dalton.

A preferred subgroup of polymeric organic materials are highly crosslinked macroporous polystyrene or polyacrylate.

The particle size of the polymeric organic materials is preferably from 10 μm to 2000 μm.

The highly crosslinked polymeric organic materials preferably have a specific surface area determined by the BET method of from 20 m²/g to 1000 m²/g, particularly preferably from 50 m²/g to 500 m²/g.

The invention further provides a process for preparing the polymeric support material of the invention, wherein polymers containing structural repeating units of at least one monomer containing a bonded hydroxyl group or a bonded primary or secondary amino group as functional group directly in the polymer backbone or in a side chain A) are, in a first step, completely or partially reacted with a diisocyanate forming a bridging group Q in an inert organic solvent and the product is, in a second step, reacted with a diphosphine in which the 1 and 2 positions of the one cyclopentadienyl ring bear tertiary phosphine groups of which one is bound directly and the other via a group $CHR_1$ to the cyclopentadienyl ring and the other cylcopentadienyl radical bears a silylene group —$Si(R_{12})_2$-$R_{13}$-A-: or B) in a first step, a diphosphine in which the 1 and 2 positions of the one cyclopentadienyl ring bear tertiary phosphine groups of which one is bound directly and the other via a group $CHR_1$ to the cyclopentadienyl ring and the other cyclopentadienyl ring bears a silylene group —$Si(R_{12})_2$-$R_{13}$-A- is completely or partially reacted with a diisocyanate forming a bridging group Q in an inert organic solvent and the product is, in a second step, completely or partially reacted with a polymer containing structural repeating units of at least one monomer containing a bonded hydroxyl group or a bonded primary or secondary amino group as functional group, where the radicals A, $R_{12}$ and $R_{13}$ are as defined above and C) any free isocyanate groups still present are crosslinked with a $C_2$–$C_{24}$diol or $C_2$–$C_{24}$diamine or are reacted with a $C_2$–$C_{12}$alcohol or $C_2$–$C_{12}$amine.

In this way, the polymer can have its properties subsequently modified in a targeted manner.

In a further process variant for preparing the polymeric support material of the invention, polymers containing structural repeating units of at least one monomer containing a bonded hydroxyl group or a bonded primary or secondary amino group as functional group A) are, in a first step, completely or partially reacted with a diisocyanate forming a bridging group Q in an inert organic solvent and the product is, in a second step, completely or partially reacted with a diphosphine in which the 1 and 2 positions of the one cyclopentadienyl ring bear tertiary phosphine groups of which one is bound directly and the other via a group $CHR_1$ to the cyclopentadienyl ring and the other cyclopentadienyl ring bears a silylene group —$Si(R_{12})_2$-$R_{13}$-A- and the free isocyanate groups still present are allowed to react with an aliphatic $C_2$–$C_{12}$alcohol or $C_2$–$C_{12}$amine.

In a likewise suitable process procedure for preparing the polymeric support material of the invention, the polymers containing structural repeating units of at least one monomer containing a bonded hydroxyl group or a bonded primary or secondary amino group as functional group A) are, in a first step, completely or partially reacted with a diisocyanate forming a bridging group Q in an inert organic solvent and the product is, in a second step, completely or partially reacted with a diphosphine in which the 1 and 2 positions of the one cyclopentadienyl ring bear tertiary phosphine groups of which one is bound directly and the other via a group $CHR_1$ to the cyclopentadienyl ring and the other cyclopentadienyl ring bears a silylene group —Si$(R_{12})_2$-$R_{13}$-A- and the free isocyanate groups still present are crosslinked with an aliphatic $C_2$–$C_{24}$diol or $C_2$–$C_{24}$diamine.

If such crosslinked polymers are prepared, preference is given to crosslinking from 0.01 to 10 mol % of the total isocyanate groups present.

The processes are preferably carded out in a polar or nonpolar aprotic solvent. The solvent is particularly preferably a halogenated hydrocarbon, an ester, a ketone, an acid amide, an ether, dimethyl sulfoxide or an unsubstituted or substituted hydrocarbon such as xylene, toluene, benzene, chlorobenzene.

The diisocyanates forming a bridging group Q can be reacted with the amine or hydroxyl groups of the polymer and of the diphosphine at room temperature or elevated temperature, for example from 30° to 100° C., using methods known from the literature. The subsequent introduction of, for example, a hydroxyl group into highly crosslinked polystyrene can be carried out by known methods. It is first chloromethylated as described in J. Mol. Catal. 51 (1989), 13–27 and subsequently saponified by the method given by J. M. Frechet et al. in Polymer, 20 (1979) 675–680.

The subsequent modification can also be carried out in bulk, for example using plasma processes. Chemical processes in solution or in emulsion are also possible.

Insoluble polymers are milled beforehand using known methods and adjusted to the desired particle size.

The invention further provides a solid inorganic material having ferrocenyldiphosphine ligands of the formula XIII bound to its surface

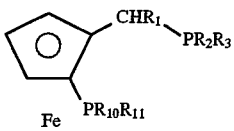

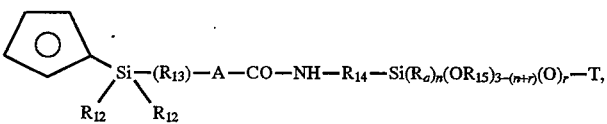

in which $R_a$, $R_1$, $R_2$, $R_3$, $R_{10}$, $R_{11}$, $R_{12}$, $R_{13}$, $R_{14}$, $R_{15}$, A and n are as defined above and T is a solid inorganic support material where r is 1, 2 or 3 when n is 0, r is 1 or 2 when n is 1 and r is 1 when n is 2.

The solid support material T can comprise silicates and semimetal or metal oxides, or glasses, which are preferably in the form of powder having mean particle diameters of from 10 nm to 2000 μm, preferably from 10 nm to 1000 μm and particularly preferably from 10 nm to 500 μm. The particles can be either compact or porous. Porous particles preferably have a high internal surface area, for example from 1 to 1200 m², preferably from 30 to 600 m². Examples of oxides and silicates are $SiO_2$, $TiO_2$, $ZrO_2$, MgO, NiO, $WO_3$, $Al_2O_3$, $La_2O_3$, silica gels, clays and zeolites. Preferred support materials are silica gels, aluminium oxide, titanium oxide or glass and mixtures thereof. An example of a glass as support material is "controlled pore glass", which is commercially available.

The materials of the formula XIII can be prepared by a method analogous to that described in EP-A-0 496 699, by allowing compounds of the formula Id

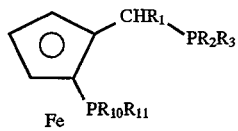

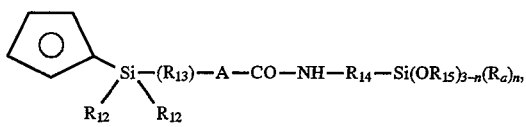

in which $R_{al}$, $R_1$, $R_2$, $R_3$, $R_{10}$, $R_{11}$, $R_{12}$, $R_{13}$, $R_{14}$, $R_{15}$, A and n are as defined above, in an inert organic solvent with a solid inorganic support material T, preferably under inert gas, for example argon, and at a temperature of from 40° to 180° C. Advantageously, a reaction vessel is initially charged with the solid material, a solution of the compound of the formula Id is added and the mixture is stirred at elevated temperature, for example from 50° to 110° C. Suitable solvents have been mentioned above, particularly preferred solvents being toluene and xylene. The product can be isolated either by decantation, centrifugation or filtration. The residue is purified by washing with an alkanol and is then added in a high vacuum.

The invention further provides rhodium or iridium complexes of inorganic or organic polymeric support materials to which are bound ferrocenyldiphosphines in which the 1 and 2 positions of the one cyclopentadienyl ring bear tertiary phosphine groups of which one is bound directly and the other via a group $CHR_1$ to the cyclopentadienyl ring and the other cyclopentadienyl radical bears a silylene group —Si $(R_{12})_2$-$R_{13}$-A-, bonded via the Si atom, which forms one end of an organic bridging group and at the other end of which the inorganic or polymeric organic support is bound via the group A, directly or via an additional group, where the radicals A, $R_{12}$ and $R_{13}$ are as defined above.

Preference is given to complexes of rhodium or iridium with the polymeric organic material of the formula XIIa or XIIb,

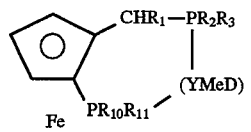

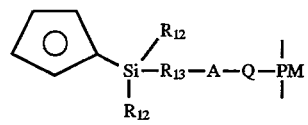

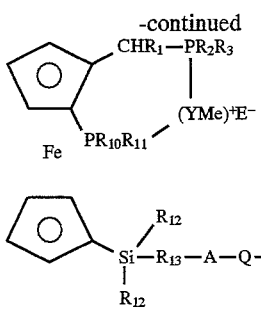

(XIIb)

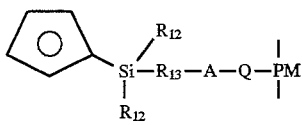

in which $R_1$, $R_2$, $R_3$, $R_{10}$, $R_{11}$, $R_{12}$, $R_{13}$, Q, PM, Y, Me, D and $E^-$ are as defined and preferred above.

The invention further provides a process for preparing metal complexes with the polymeric support material, wherein compounds of the formula XI are reacted with a metal compound of the formula $[M(Y)D]_2$ or $M(Y)_2^+E^-$, in which M is rhodium or iridium and Y, D and $E^-$ are as defined above.

The reaction is advantageously carried out under an inert gas atmosphere, for example argon, and conveniently at temperatures of from 0° to 40° C., preferably at room temperature, if the polymer-bonded diphosphines are soluble. Concomitant use is advantageously made of a solvent or mixture of solvents, for example hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, ethylene glycol dimethyl ether) or mixtures thereof.

A precalculated amount of this catalyst solution can be used directly for a hydrogenation reaction. The polymer-bonded catalyst can also be isolated in solid form by evaporation of the solvent or by addition of a solvent in which the polymer is insoluble.

It is also possible to prepare the catalyst in situ directly in the hydrogenation solution. In the case of insoluble, partially or highly crosslinked polymer-bonded diphosphines, the metal compounds of the formula $[Me(Y)Z]_2$ or $Me(Y)_2^+A^-$ are first dissolved in a solvent and this solution is added to the dissolved or slurried material. This can be carried out using the above described reaction conditions. The polymer of the invention can either be used directly or be isolated by filtration, purified by washing with the abovementioned solvents and dried in vacuo.

The invention also provides rhodium or iridium complexes of the formula XIIIa and XIIIb of the solid inorganic material of the formula XIII

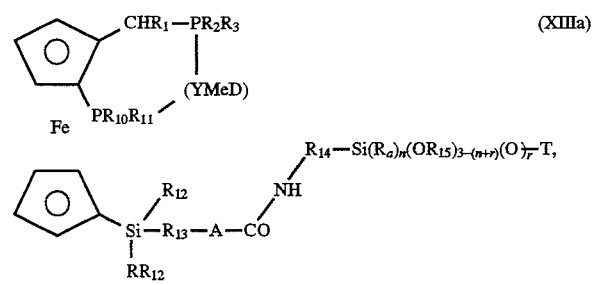

(XIIIa)

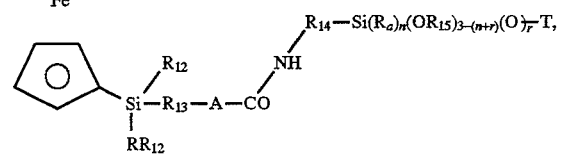

(XIIIb)

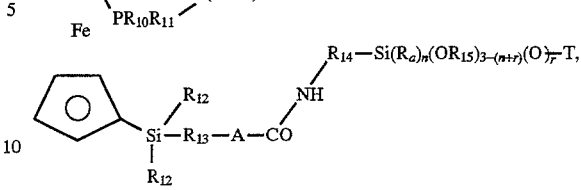

in which A, $R_a$, $R_1$, $R_2$, $R_3$, $R_{10}$, $R_{11}$, $R_{12}$, $R_{13}$, $R_{14}$, $R_{15}$, Y, Me, D, $E^-$, r, n and T are as defined and preferred above.

The reaction conditions described for the preparation of metal complexes containing polymeric support material can be used.

The reaction is advantageously carried out in a inert gas atmosphere, for example argon, and conveniently at temperatures of from 0° to 40° C., preferably at room temperature. Concomitant use is advantageously made of a solvent or mixture of solvents, for example hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, ethylene glycol dimethyl ether) or mixtures thereof.

The inorganic metal complexes of the invention can also be prepared in situ prior to a hydrogenation and can then be used directly as hydrogenation catalysts.

The organic polymeric and inorganic metal complexes of the invention are very useful as catalysts for hydrogenating organic double and triple bonds. For example, compounds containing the groups C=C, C=N, C=O, C=C—N or C=C—O are obtained (see, for example, K. E. König, The Applicability of Asymmetric Homogeneous Catalysis, in James D. Morrison (ed.), Asymmetric Synthesis, Vol. 5, Academic Press, 1985). In particular, the organic polymeric and inorganic metal complexes of the invention are suitable for the enantioselective hydrogenation of compounds containing prochiral carbon-carbon and carbon-heteroatom double bonds. Examples of such compounds are prochiral alkenes, imines and ketones. After the reaction, the catalysts of the invention can be virtually completely separated off from the reaction mixture in a simple manner, for example by decantation, centrifugation or filtration.

The invention accordingly further provides for the use of the novel complexes of rhodium or iridium as heterogeneous or homogeneous catalysts for the assymetric hydrogenation of prochiral compounds containing carbon-carbon or carbon-heteroatom double bonds.

The metal complexes are preferably used for the assymetric hydrogenation of prochiral compounds containing carbon-carbon or carbon-heteroatom double bonds, in particular the Ir complexes for the hydrogenation of assymetric ketimines.

The invention further provides a process for the assymetric hydrogenation of compounds containing carbon-carbon or carbon-heteroatom double bonds, wherein the compounds are reacted at a temperature of from $-20°$ to $80°$ C. and a hydrogen pressure of from $10^5$ to $2\times10^7$ Pa in the presence of catalytic amounts of one or more novel metal complexes of the formulae XIIa, XIIb, XIIIa and XIIIb.

The examples below illustrate the invention
General procedures in the syntheses:

Unless stated otherwise, all reactions are carried out under inert gas and using degassed solvents. The column chromatography is in each case carried out using silica gel 60 from Merck.

Abbreviations used in the experimental description are:

TMEDA: N,N,N,N-tetramethylethylenediamine

BPPFA: N,N-dimethyl-1-[1',2-bis(diphenylphosphino)ferrocenyl]ethylamine

DMF: N,N-dimethylformamide

COD: 1,5-cyclooctadiene

Synthesis of the intermediates:

EXAMPLE A1

Synthesis of (R)-N,N-dimethyl-1-[1'-(1"-dimethylsilyl-3"-chloropropyl)-(S)-2-diphenylphosphinoferrocenyl]ethylamine (2):

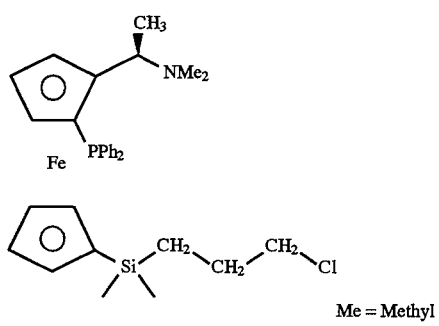

Me = Methyl 32.5 ml of a 1.6 molar solution of butyllithium in hexane (52 mmol) are added dropwise while stirring at room temperature to a solution of 10.29 g (40 mmol) of (R)-N,N-dimethyl-1-ferrocenylethylamine in 50 ml diethyl ether. After stirring for one hour, a further solution comprising 35.6 ml of a 1.6 molar solution of butyllithium in hexane (57 mmol) and 7.5 ml of TMEDA (50 mmol) is added dropwise and the reddish brown reaction solution is stirred for a further 5 hours. Subsequently, at about −20° C., a solution comprising a mixture of 7.4 ml of chlorodiphenylphosphine (40 mmol) and 22.9 ml of 3-chloropropyldimethylchlorosilane (140 mmol) is added dropwise. The reaction mixture is subsequently stirred overnight at room temperature.

Work-up: the reaction mixture is slowly treated at 0° C. with 10 ml of saturated $NaHCO_3$ solution and subsequently with 100 ml of water and is shaken 3 times with 50 ml each time of ethyl acetate. The organic phase is extracted with 50 ml of water, dried with $Na_2SO_4$ and evaporated under reduced pressure (10–20 torr) on a rotary evaporator. The excess, hydrolysed chlorosilane is then distilled off from the crude product under a high vacuum (about 0.01 torr) at a bath temperature of up to 70° C. Rough column chromatography (eluant=hexane/acetic acid) gives 15.4 g of a mixture of the (R)-(S) compound of the formula II and some BPPFA. The BPPFA can be removed by crystallization from methanol/ethanol 1:1. This gives 13.5 g of product having a purity of 95% (yield: 55%, reddish brown high-viscosity oil).

Characterization:

$^{31}P$- NMR ($CDCl_3$): δ -23.71

$^1H$-NMR ($CDCl_3$): δ 0.05(s, 3H, Si—$CH_3$), 0.15 (s, 3H, Si—$CH_3$), 0.6 (m, 2H, $CH_2$—Si) 1.28 (d, 3H, J 7 Hz, CH—$CH_3$), 1.5–1.9 (m, 2H, $CH_2$—$CH_2$—Cl), 1.78 (s, 6H, N($CH_3$)$_2$), 3,4(t,2H, J 7 Hz, $CH_2$—Cl), 3.5–4.4 (m, 8H, $C_5H_4FeC_5H_3CH$), 7.1–7.7 (m, 10H, P($C_6H_5$)$_2$).

Starting from (S)-N,N-dimethyl-1-ferrocenylethylamine, the compound of the formula 2 having the (S)-(R) configuration is prepared in a similar manner.

EXAMPLES A2

Synthesis of the compounds of the formulae 3a, 3b, 3c:

All the following syntheses are carded out starting from the compound of the formula 2 in the (R)-(S) configuration and give the corresponding (R)-(S)ligands.

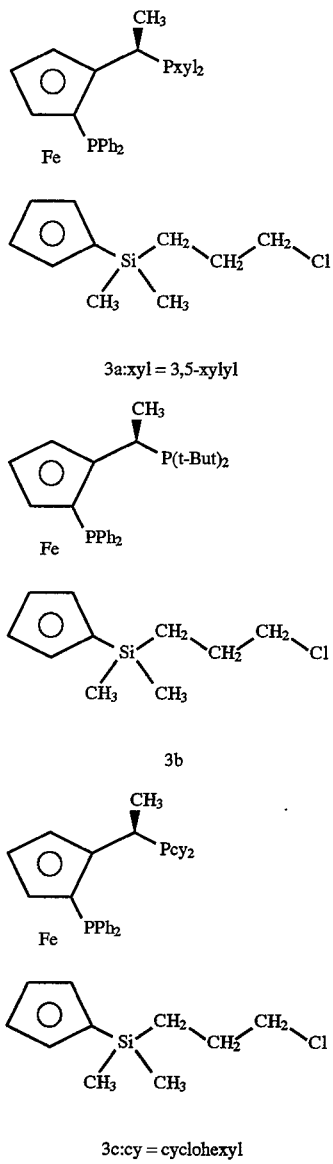

3a:xyl = 3,5-xylyl

3b

3c:cy = cyclohexyl

EXAMPLE A2

Synthesis of (R)-1-[1'-(1"-dimethylsilyl-3"-chloropropyl)-(S)-2-diphenylphosphinoferrocenyl]ethyldi-3,5-xyl-1-ylphosphine 3a:

1.12 g (4.6 mmol) of bis(3,5-xylyl)phosphine in 5 ml of acetic acid are added to 2.66 g (4.6 mmol) of the compound prepared in Example A1 in 10 ml of acetic acid and the mixture is stirred for 90 minutes at 5° C. in an oil bath. After cooling, the reddish brown solution is shaken with 30 ml of toluene and 100 ml of a 5% aqueous NaCl solution. The aqueous phase is then shaken 3 times with 15 ml of toluene. The organic phases are then collected, washed with 50 ml of water, dried with $Na_2SO_4$ and evaporated under reduced pressure on a rotary evaporator. The crude product is purified by column chromatography (eluant: hexane/diethyl ether). This gives 1.85 g of 3a (orange powder, yield: 52%).

Characterization:

$^{31}$P- NMR (CDCl$_3$): δ - 25.46 (d, PPh$_2$), 6.65 (d, Pxyl$_2$), JPP 21 Hz.

EXAMPLE A2b

Synthesis of (R)-1-[1'-(1''-dimethylsilyl-3''-chloropropyl)-(S)-2-diphenylphosphinoferrocenyl]ethyldi-tert-butylphosphine 3b.

The compound is prepared from 2.18 g (3.79 mmol) of 2 and 560 mg (3.8 mmol) of di-tert-butylphosphine by a method similar to Example A2a and is purified by column chromatography (eluant: hexane/diethyl ether). This gives 1.97 g of product (reddish brown, almost solid oil, yield: 77%).

Characterization:

$^{31}$P- NMR (CDCl$_3$): δ - 26.6 (d, PPh$_2$), 50.4 (d, P(t-But)$_2$), JPP 54 Hz.

EXAMPLE A2c

Synthesis of (R)-1-[1'-(1''-dimethylsilyl-3''-chloropropyl)-(S)-2-diphenylphosphinoferrocenyl]ethyldicyclohexylphosphine 3c.

The compound is prepared from 1.5 g (2.6 mmol) of 2 and 0.54 ml (2.65 mmol) of dicylcohexylphosphine by a method similar to Example A2a and is purified by column chromatography (eluant: hexane/diethyl ether). This gives 1.42 g of product (brown powder, yield: 75%).

Characterization:

$^{31}$P-NMR (CDCl$_3$): δ - 26.5 (d, PPh$_2$), 15.8 (d, Pcy$_2$), JPP 34 Hz.

EXAMPLE A3

Synthesis of the primary amines of the formulae 5a–c:

The primary amines are prepared by Gabriel syntheses (reaction of the chloride to give the phthalimide and setting free of the amine using hydrazine hydrate):

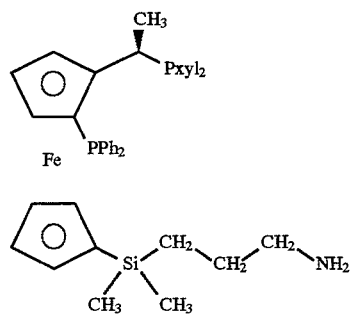

5a:xyl = 3,5-xylyl

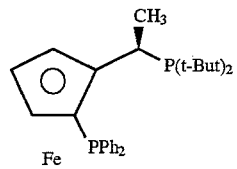

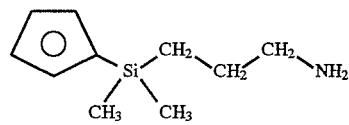

5b

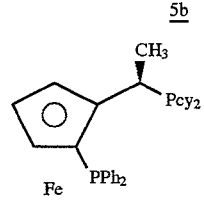

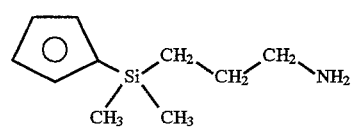

5c:cy = cyclohexyl

EXAMPLE A3a 492 mg of potassium phthalimide and 130 mg of hexadecyltributylphosphonium bromide (catalyst) are added to a solution of 1.64 g (2.1 mmol) of the compound of the formula 3a from Example A2a in 2 ml of DMF and the mixture is stirred for 2.5 hours at 96° C. After cooling, the mixture is shaken with water/toluene, the organic phase is dried with sodium sulfate and evaporated on a rotary evaporator. Chromatographic purification (eluant: hexane/ethyl acetate) gives 1.8 g of orange powder (yield: 96%).

Characterization:

$^{31}$P- NMR (CDCl$_3$): δ - 25.33 (d, PPh$_2$), 6.97 (d, Pxyl$_2$), JPP 22 Hz.

$^1$H-NMR (CDCl$_3$): δ characteristic signals 3.6 (t, 2H, J=7, CH$_2$-N), 7.6–7.9 (m, 4H, phthalimide).

1.8 g (2.04 mmol) of the orange powder and 0.4 ml of hydrazine hydrate in 20 ml of ethanol are heated under reflux for 4 hours. After cooling, 50 ml of methylene chloride are added, the suspension is filtered and washed. The solution is evaporated under reduced pressure on a rotary evaporator, the product is again slurried with 50 ml of methylene chloride and filtered. Evaporation on a rotary evaporator gives 1.5 g of orange powder of the compound of the formula 5a (yield: 97%).

Characterization:

$^{31}$P- NMR (CDCl$_3$): δ - 25.38 (d, PPh$_2$), 6.6 (d, Pxyl$_2$), JPP 22 Hz.

$^1$H-NMR (CDCl$_3$): δ characteristic signals 2.58 (t, 2H, J=7, CH$_2$-N).

EXAMPLE A3b 800 mg of potassium phthalimide and 14 mg of hexadecyltributylphosphonium bromide (catalyst) are added to a solution of 2 g (2.9 mmol) of the compound of the formula 3b from Example A2b in 5 ml of DMF and the mixture is stirred for 11 hours at 96° C. After cooling, the mixture is shaken with water/toluene, the organic phase is dried with sodium sulfate and evaporated on a rotary evaporator. Chromatographic purification (eluant: hexane/ethyl acetate) gives 2.15 g of orange powder (yield: 94%).

Characterization:

$^{31}$P- NMR (CDCl$_3$): δ - 26.7 (d, PPh$_2$), 50.2 (d, P(t-But)$_2$), JPP 54 Hz.

$^1$H-NMR (CDCl$_3$): δ characteristic signals 3.6 (t, 2H, J=7, CH$_2$-N), 7.6–7.9 (m, 4H), phthalimide).

2.1 g (2.67 mmol) of the orange powder and 0.5 ml of hydrazine hydrate are refluxed in 20 ml of ethanol for 2 hours. After cooling, 50 ml of methylene chloride are added, the suspension is filtered and washed. The solution is evaporated under reduced pressure on a rotary evaporator, the product is slurried with 15 ml of diethyl ether, filtered and washed again. Evaporation on a rotary evaporator gives 1.7 g of orange, almost solid oil of the compound of the formula 5b (yield: 97%).

Characterization:

$^{31}$P- NMR (CDCl$_3$): δ - 26.6 (d, PPh$_2$), 50.3 (d, P(t-But)$_2$), JPP 54 Hz.

$^1$H-NMR (CDCl$_3$): δ characteristic signals 2.6 (t, 2H, J=7, CH$_2$-N).

EXAMPLE A3c 450 mg of potassium phthalimide and 120 mg of hexadecyltributylphosphonium bromide (catalyst) are added to a solution of 1.4 g (1.94 mmol) of the compound of the formula 3c from Example A2c in 3 ml of DMF and the mixture is stirred for 1.5 hours at 96° C. After cooling, the mixture is shaken with water/toluene, the organic phase is dried with sodium sulfate and evaporated on a rotary evaporator. Chromatographic purification (eluant: hexane/ethyl acetate) gives 1.32 g of orange powder (yield: 81%).

Characterization:

$^{31}$P- NMR (CDCl$_3$): δ - 26.5 (d, PPh$_2$), 15.8 (d, Pcy$_2$), JPP 34 Hz.

$^1$H-NMR (CDCl$_3$): δ characteristic signals 3.58 (t, 2H, J=7, CH$_2$-N), 7.6–7.9 (m, 4H, phthalimide).

1.24 g (1.48 mmol) of the orange powder and 0.3 ml of hydrazine hydrate in 12 ml of ethanol are heated under reflux for 2 hours. After cooling, 25 ml of methylene chloride are added, the suspension is filtered and washed. The solution is evaporated under reduced pressure on a rotary evaporator, and the product is purified by chromatography (eluant: MeOH containing 2% of triethylamine). This gives 0.98 g of orange, almost solid oil of the compound of the formula 5c (yield: 94%).

Characterization: $^{31}$P- NMR (CDCl$_3$): δ - 26.5 (d, PPh$_2$), 15.7 (d, Pcy$_2$), JPP 33 Hz.

$^1$H-NMR (CDCl$_3$): δ characteristic signals 2.6 (t, 2H, J=7, CH$_2$-N).

EXAMPLE A4

Preparation of the secondary amine of the formula 6a:

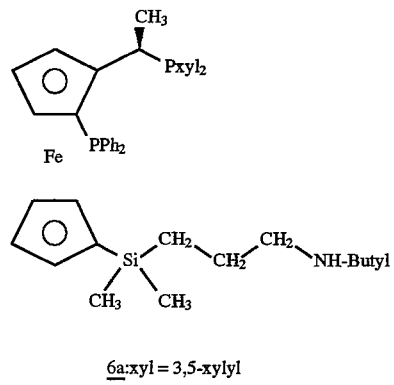

6a:xyl = 3,5-xylyl 400 mg (0.518 mmol) of the compound of the formula 3a from Example A2a are heated under reflux in the presence of 12 mg of tetrabutylammonium iodide for 20 hours in 5 ml of n-butylamine. The butylamine is subsequently distilled off under reduced pressure and the mixture is shaken with water/ethyl acetate. The organic phase is dried with Na$_2$SO$_4$, evaporated on a rotary evaporator and the crude product is purified by chromatography (eluant: ethyl acetate containing 2% of triethylamine). This gives 0.38 g of an orange, viscous oil of the compound of the formula 6a (yield: 88%).

Characterization:

$^{31}$P- NMR (CDCl$_3$): δ - 25.1 (d, PPh$_2$), 6.8 (d, Pxyl$_2$), JPP 21 Hz.

$^1$H-NMR (CDCl$_3$): δcharacteristic signals 0.9 (t, 3H, J=7, CH$_2$–CH$_3$), 2.45–2.6 (m, 4H, two CH$_2$-N).

EXAMPLE A5

Synthesis of the ligands of the formulae 7a–c and 8a capable of being immobilized on inorganic supports:

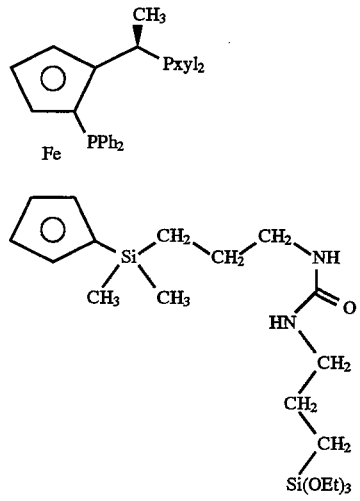

7a:xyl = 3,5-xylyl

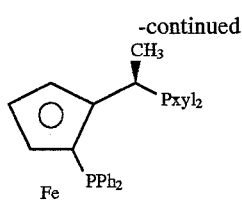

8a

7b

7c: cy = cyclohexyl

EXAMPLE A5a 0.65 ml (2.46 mmol) of 1-triethoxysilyl-3-isocyanatopropane are added dropwise to a solution of 1.48 g (1.97 mmol) of the compound of the formula 5a from Example A3a in 20 ml of methylene chloride and the mixture is stirred overnight at room temperature. The solvent is subsequently taken off under reduced pressure on a rotary evaporator and the crude product is purified by chromatography (eluant: hexane/ethyl acetate). This gives 1.45 g of an orange, viscous foam of the compound of the formula 7a (yield: 74%).

Characterization: $^{31}$P- NMR (CDCl$_3$): δ - 25.2 (d, PPh$_2$), 6.7 (d, Pxyl$_2$), JPP 21 Hz.

$^1$H-NMR (CDCl$_3$): δ 1.22 (t, J=7, 9H, O—CH$_2$—CH$_3$), 3.81 (q, J=7, 6H, O—CH$_2$).

EXAMPLE A5b 0.3 ml (1.15 mmol) of 1-triethoxysilyl-3-isocyanatopropane is added dropwise to a solution of 602 mg (0.91 mmol) of the compound of the formula 5b from Example A3b in 10 ml of methylene chloride and the mixture is stirred overnight at room temperature. The solvent is subsequently taken off under reduced pressure on a rotary evaporator and the crude product is purified by chromatography (eluant: hexane/ethyl acetate). This gives mg of an orange, viscous foam of the compound of the formula 7b (yield: 72%).

Characterization:

$^{31}$P- NMR (CDCl$_3$): δ - 26.7 (d, PPh$_2$), 50.2 (d, P(t-But)$_2$), JPP 55 Hz.

$^1$H-NMR (CDCl$_3$): δ 1.22 (t, J=7, 9H, O—CH$_2$—CH$_3$), 3.81 (q, J=7, 6H, O—CH$_2$).

EXAMPLE A5c 0.24 ml (0.9 mmol) of 1-triethoxysilyl-3-isocyanatopropane is added dropwise to a solution of 506 mg (0.71 mmol) of the compound of the formula 5c from Example A3c in 10 ml of methylene chloride and the mixture is stirred overnight at room temperature. The solvent is subsequently taken off under reduced pressure on a rotary evaporator and the crude product is purified by chromatography (eluant: ethyl acetate). This gives 530 mg of an orange, viscous foam of the compound of the formula 7c (yield: 72%).

Characterization:

$^{31}$P- NMR (CDCl$_3$): δ - 26.5 (d, PPh$_2$), 15.7 (d, Pcy$_2$), JPP 33 Hz.

$^1$H-NMR (CDCl$_3$): δ 1.22 (t, J=7, 9H, O—CH$_2$—CH$_3$), 2.95–3.25 (m, 4H, CH$_2$—NH—C(O)—NH—CH$_2$) 3.81 (q, J=7, 6H, O—CH$_2$).

EXAMPLE A5d 0.1 ml (0.37 mmol) of 1-triethoxysilyl-3-isocyanatopropane is added dropwise to a solution of 251 mg (0.31 mmol) of the compound of the formula 6a from Example A4 in 4 ml of methylene chloride and the mixture is stirred for 2.5 hours at room temperature. The solvent is subsequently taken off under reduced pressure on a rotary evaporator and the crude product is purified by chromatography (eluant: hexane/ethyl acetate). This gives 230 mg of an orange, viscous oil of the compound of the formula 8a (yield: 70%).

Characterization:

$^{31}$P- NMR (CDCl$_3$): δ - 25.3 (d, PPh$_2$), 6.7 (d, Pxyl$_2$), JPP 21 Hz.

$^1$H-NMR (CDCl$_3$): δ characteristic signals 0.9 (t, 3H, J=7, CH$_2$-CH$_3$), 1.22 (t, J=7, 9H, O—CH$_2$—CH$_3$).

EXAMPLE B

Ligands immobilized on silica gel;

Immobilization: Before use, the support material is in each case dried at 130° C. for 3 hours under a high vacuum and subsequently placed under argon. A solution in toluene of the ligand to be immobilized from Example A5 is then added and the mixture is stirred for 20 hours at 85°–90° C. After cooling and settling, the supernatant solution is drawn off using a syringe. The mixture is subsequently washed 6 times with MeOH (in each case 7 ml per g of support) and subsequently dried at 40°–50° C. in a high vacuum. The results are shown in Table 1.

manipulations are carried out under inert gas. The hydrogenations are carried out in a 50 ml glass flask provided with a magnetic stirrer (1500 rpm), an inert gas connection and a rubber septum. The reagents and the hydrogen are introduced using syringes and needles. The hydrogenations of Examples E1 and E2 using the rhodium complexes are carried out under hydrogen at atmospheric pressure. Prior to the hydrogenation, the inert gas in the autoclave is displaced by hydrogen, in each case in 4 cycles (vacuum, hydrogen at atmospheric pressure). The hydrogenation is started by switching on the stirrer. The conversion is determined in each case by the hydrogen consumption or by means of $^1$H-NMR and the optical yield is determined by means of HPLC (column: Chiracel 0 J).

TABLE 1

| No. | Immobilizable ligand No. | Amount [mg] | Support type | Amount [g] | Amount of toluene [ml] | P content by analysis [%] | mmol of ligand Immobilized on 1 g of support |
| --- | --- | --- | --- | --- | --- | --- | --- |
| B1 | 7a | 400 | Grace 332 | 3.3 | 15 | 0.59 | 0.095 |
| B2 | 7a | 300 | Grace 332 | 6.3 | 28 | 0.25 | 0.04 |
| B3 | 7a | 120 | Grace 332 | 7.5 | 38 | 0.08 | 0.013 |
| B4 | 7b | 290 | Grace 332 | 3 | 13.5 | 0.62 | 0.1 |
| B5 | 7b | 181 | Grace 332 | 5 | 22.5 | 0.27 | 0.043 |
| B6 | 7c | 238 | Grace 332 | 2.2 | 9.8 | 0.61 | 0.098 |
| B7 | 7c | 100 | Grace 332 | 2.2 | 9.8 | 0.26 | 0.041 |
| B8 | 8a | 80 | Grace 332 | 2 | 9 | 0.18 | 0.028 |
| B9 | 8a | 60 | Grace 500A | 6 | 26 | 0.04 | 0.007 |

Support used from W. R. Grace: Grace 332: specific surface area = 320 m$^2$/g, particle size = 35–70 μm. Grace 500A: controlled pore glass, specific surface area = 80 m$^2$/g, pore diameter = 50 nm.

EXAMPLE C

Polymer-bonded ligands

EXAMPLE C1

Immobilization of the ligand of the formula 5a from Example A3a on functionalized polystyrene.

In a vessel fitted with a stirrer and a frit, 930 mg of polymer (aminomethylated polystyrene, crosslinked with 1% of divinylbenzene, amine content=0.56 mmol/g, from Novabiochem), which has been dried in a high vacuum at 50° C., are stirred in 35 ml of methylene chloride until the support material is swollen. 1.2 ml (8.3 mmol) of tolylene 2,4-diisocyanate (TDI) are then quickly added and the mixture is stirred further for 1 hour. The excess TDI is subsequently removed by filtering the solution and washing 5 times with 30 ml of methylene chloride. The support reacted with TDI is then stirred in 30 ml of methylene chloride and a solution of 94 mg (0.125 mmol) of the compound of the formula 5a from Example A3a in 2 ml of methylene chloride is added dropwise. The mixture is stirred overnight. To convert the remaining isocyanate groups into carbamates, 10 ml of ethanol containing 30 μl of triethylamine as catalyst are added and the mixture is stirred for 8 hours at 40° C. The yellow-orange support is then filtered off and washed 5 times with 20 ml each time of methylene chloride. It is finally dried in a high vacuum.

Analysis: P content=0.59%. This corresponds to 0.095 mmol of ligand immobilized on 1 g of support.

EXAMPLE E

Preparation of N-(2',6'-dimethylphen-1'-yl)-N-(methoxyacetyl)-1-methoxycarbonylethylamine Use of the ligands from Examples B6 and B7. Hydrogenation using rhodium complexes. General procedures: all

EXAMPLE E1

A solution of 4.06 mg of [Rh(COD)$_2$]BF$_4$ in 3.3 ml of methanol is added to 122 mg of the ligand from Example B6 (ligand 7c) and the mixture is slowly stirred, with the yellow solution becoming decolorized. 554 mg of substrate (N-(2', 6'-dimethylphen-1'-yl)-N-(methoxyacetyl)-1-methoxycarbonylethenylamine) dissolved in 5 ml of methanol are then added, the mixture is heated to 40° C. in an oil bath and is hydrogenated at this temperature. The reaction is stopped after I hour and the hydrogen in the hydrogenation flask is replaced by inert gas. The catalyst is allowed to settle and the supernatant solution is drawn off using a syringe. The conversion is quantitative and the optical yield is 82.2% (R). Reuse: A solution of 554 mg of substrate in 8.3 ml of methanol is again added to the separated-off catalyst from Example E1, the mixture is again heated to 40° C. and is hydrogenated at this temperature. The reaction is stopped after 1 hour and the catalyst is filtered off. The conversion is quantitative and the optical yield is 81.7% (R). Rh analysis: the Rh content of the reaction solution is below the detection limit (3 ppm) of the measurement method used. This means that more than 98% of the catalyst used is recovered.

EXAMPLE E2

A solution of 4.06 mg of [Rh(COD)$_2$]BF$_4$ in 3.3 ml of methanol is added to 122 mg of the ligand from Example B7 and the mixture is slowly stirred, with the yellow solution becoming decolorized. 554 mg of substrate (N-(2',6'-dimethylphen-1'-yl)-N-(methoxyacetyl)-1-methoxycarbonylethenylamine) dissolved in 5 ml of methanol are then added, the mixture is heated to 40° C. in an oil bath and is hydrogenated at this temperature. The reaction is stopped after I hour and the hydrogen in the hydrogenation flask is replaced by inert gas. The catalyst is allowed to settle and the supernatant solution is drawn off using a syringe. The conversion is quantitative and the optical yield is 80.9% (R). Reuse: A solution of 554 mg of substrate in 8.3 ml of methanol is again added to the separated-off catalyst from Example E2, the mixture is again heated to 40° C. and is hydrogenated at this temperature. The reaction is stopped after 1 hour and the catalyst is filtered off. The conversion is quantitative and the optical yield is 80% (R). Rh analysis: the Rh content of the reaction solution is below the detection limit (3 ppm) of the measurement method used. This means that more than 98% of the catalyst used is recovered.

Examples E3 to E5; imine hydrogenation using iridium complexes.

Preparation of N-(2'-methyl-6'-ethylphen-1'yl)-N-(1-methoxymethyl)ethylamine

General: All manipulations are carried out under inert gas. The 50 ml steel autoclave is equipped with a magnetic stirrer (1500 rpm) and baffles. Prior to the hydrogenation, the inert gas in the autoclave is displaced by hydrogen, in each case in 4 cycles (10 bar, atmospheric pressure). The desired hydrogen pressure in the autoclave is then set and the hydrogenation is started by switching on the stirrer. The conversion is in each case determined by gas chromatography and the optical yield is determined by means of HPLC (column: Chiracel OD), using a sample purified by flash chromatography (silica gel Merck 60, eluant=hexane/ethyl acetate).

EXAMPLE E3

A solution of 3.3 mg of [Ir(COD)Cl]$_2$ (0.0097 mmol of Ir) in 2 ml of THF are added all at once to 260 mg (0.0118 mmol) of ligand B2 and the mixture is stirred slowly, with the yellow solution becoming decolorized. The catalyst is then allowed to settle, the supernatant THF is drawn off using a syringe and the catalyt is dried in a high vacuum. A second flask is charged with 9.6 mg of tetrabutylammonium iodide and finally 4 g (19.5 mmol) of N-(2'-methyl-6'-ethylphen-1'-yl)-N-(1-methoxymethyl)ethylimine, the solution is placed under inert gas and is added to the catalyst. The reaction mixture is then injected using a steel capillary under a countercurrent of inert gas into a 50 ml steel autoclave and subsequently hydrogenated at 25° C. under a hydrogen pressure of 80 bar. After 2 hours, the hydrogen is vented and the catalyst is filtered off under argon. The conversion is quantitative, the optical yield is 76.8% (S).

Reuse:

4 g (19.5 mmol) of N-(2'-methyl-6'-ethylphen-1'-yl)-N-(1-methoxymethyl)ethylimine and 9.6 mg of tetrabutylammonium iodide are added all at once to the separated-off catalyst. The reaction mixture is then injected using a steel capillary under a countercurrent of inert gas into a 50 ml steel autoclave and subsequently hydrogenated at 25° C. under a hydrogen pressure of 80 bar. After 2 hours, the hydrogen is vented and the catalyst is filtered off under argon. The conversion is quantitative, the optical yield is 77.1% (S).

EXAMPLE E4

A solution of 1.65 mg of [Ir(COD)Cl]$_2$ (0.0049 mmol of Ir) in 2 ml of THF are added all at once to 130 mg (0.0059 mmol) of ligand B2 and the mixture is stirred slowly, with the yellow solution becoming decolorized. The catalyst is then allowed to settle, the supernatant THF is drawn off using a syringe and the catalyt is added in a high vacuum. A second flask is charged with 24 mg of tetrabutylammonium iodide and finally 10 g (19.5 mmol) of N-(2'-methyl-6'-ethylphen-1'-yl)-N-(1-methoxymethyl)ethylimine, the solution is placed under inert gas and is added to the catalyst. The reaction mixture is then injected using a steel capillary under a countercurrent of inert gas into a 50 ml steel autoclave and subsequently hydrogenated at 25° C. under a hydrogen pressure of 80 bar. After 3 hours, the hydrogenation is stopped by venting the hydrogen. The catalyst is filtered off. The conversion after this time is 54%, the optical yield is 77.9% (S).

EXAMPLE E5

60 mg (0.0059 mmol) of ligand C$_1$ are stirred for 5 minutes in 2 ml of THF. A solution of 1.6 mg of [Ir(COD)Cl]$_2$ (0.0049 mmol of Ir) in 2 ml of THF is then added and stirred slowly, with the yellow solution becoming decolorized. A second flask is charged with 4.8 mg of tetrabutylammonium iodide and 2 g (9.8 mmol) of N-(2'-methyl-6'-ethylphen-1'-yl)-N-(1-methoxymethyl)ethylimine, the solution is placed under inert gas and added to the catalyst. The reaction mixture is then injected using a steel capillary under a countercurrent of inert gas into a 50 ml steel autoclave and subsequently hydrogenated at 25° C. under a hydrogen pressure of 80 bar. After 16 hours, the hydrogenation is stopped, the hydrogen is vented and the catalyst is filtered off. The conversion after this time is 62%, the optical yield is 70.3%(S).

What is claimed is:

1. A compound of the formula I

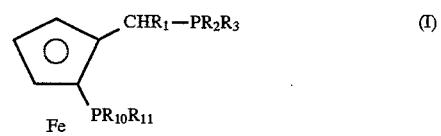

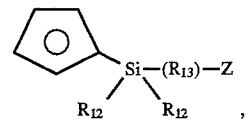

in which

R$_1$ is C$_1$–C$_8$alkyl, phenyl or phenyl substituted by from 1 to 3 C$_1$–C$_4$alkyl or C$_1$–C$_4$alkoxy groups;

R$_2$, R$_3$, R$_{10}$ and R$_{11}$, are independently of one another, C$_1$–C$_{12}$alkyl, C$_5$–C$_{12}$cycloalkyl, phenyl, C$_5$–C$_{12}$cycloalkyl substituted by C$_1$–C$_4$alkyl or C$_1$–C$_4$alkoxy, or phenyl substituted by from one to three C$_1$–C$_4$alkyl, C$_1$–C$_4$alkoxy, —SiR$_4$R$_5$R$_6$, halogen, —SO$_3$M, CO$_2$M, —PO$_3$M, —NR$_7$R$_8$, –[NR$_7$R$_8$R$_9$]X$^{+ \, or \,}$C$_1$–C$_5$fluoroalkyl groups; or the groups —PR$_2$R$_3$ and —PR$_{10}$R$_{11}$ are each, independently of one another, a radical of the formula II, IIa, IIb or IIc

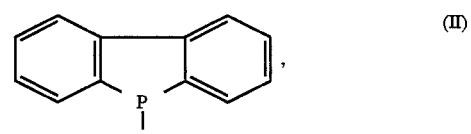

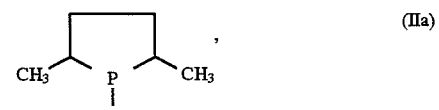

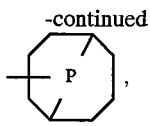  (IIb)

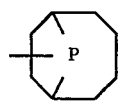  (IIc)

and $R_4$, $R_5$ and $R_6$ are, independently of one another, $C_1$–$C_{12}$alkyl or phenyl;

$R_7$ and $R_8$ are H, $C_1$–$C_{12}$alkyl, phenyl or $R_7$ and $R_8$ are together tetramethylene, pentamethylene or 3-oxa-1,5-pentylene, $R_9$ is H or $C_1$–$C_4$alkyl;

$R_{12}$ are identical or different radicals and are, independently of one another, $C_1$–$C_{12}$alkyl, $C_3$–$C_7$cycloalkyl, benzyl or phenyl or together are $C_5$–$C_{12}$alkylene and $R_{13}$ is $C_1$–$C_{12}$alkylene or phenylene, M is H or an alkali metal, $X^-$ is the anion of a monobasic acid, Z is Cl, $NH_2$, NH—$C_1$—$C_{12}$alkyl, or a group —A—CO—NH—$R_{14}$—$Si(R_a)_n$ $(OR_{15})_{3-n}$, in which A is NH or $N(C_1$–$C_{12}$alkyl), $R_{14}$ is $C_1$–$C_{12}$alkylene, $R_{15}$ is $C_1$–$C_{12}$alkyl, $R_a$ is $C_1$–$C_4$alkyl or $OR_{15}$, n is 0, 1 or 2;

and the compound of the formula I is in the form of its racemates and diastereomers or a mixture of diastereomers.

2. A compound of the formula I according to claim 1, wherein $R_1$ is linear alkyl.

3. A compound of the formula I according to claim 2, wherein $R_1$ is methyl or ethyl.

4. A compound of the formula I according to claim 1, wherein $R_1$ is phenyl or phenyl substitued by 1 or 2 $C_1$–$C_4$alkyl or $C_1$–$C_4$alkoxy groups.

5. A compound of the formula I according to claim 1, wherein $R_2$, $R_3$, $R_{10}$ and $R_{11}$ are, independently of one another, $C_1$–$C_8$alkyl.

6. A compound of the formula I according to claim 5, wherein $R_2$ and $R_3$ are identical and are i-propyl or t-butyl.

7. A compound of the formula I according to claim 1, wherein $R_2$, $R_3$, $R_{10}$ and $R_{11}$ are cycloalkyl and contain from 5 to 8 C atoms.

8. A compound of the formula I according to claim 1, wherein $R_2$, $R_3$, $R_{10}$ and $R_{11}$ are, independently one of another, unsubstituted phenyl or phenyl substituted by 1, 2 or 3 substituents.

9. A compound of the formula I according to claim 8, wherein substitued phenyl $R_2$, $R_3$, $R_{10}$ and $R_{11}$ are 2-methyl-, 3-methyl-, 4-methyl-, 2- or 4-ethyl-, 2- or 4-i-propyl-, 2- or 4-t-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-3,5-dimethyl-4-methoxy-, 3,5-dimethyl-4-(dimethylamino)-, 2- or 4-amino-, 2- or 4-methylamino-, 2- or 4-(dimethylamino) -, 2- or 4-$SO_3H$-, 2- or 4-$SO_3Na$-, 2- or 4-[$^+NH_3^-$]-, 3,4,5-trimethylphen-1-yl, 2,4,6-trimethylphen-1-yl, 4-trifluoromethylphenyl or 3,5-di(trifluoromethyl)phenyl.

10. A compound of the formula I according to claim 1, wherein $R_2$ and $R_3$ are identical and are phenyl, cyclohexyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl.

11. A compound of the formula I according to claim 1, wherein $R_2$ and $R_3$ are identical and are cylcohexyl or phenyl.

12. A compound of the formula I according to claim 1, wherein $R_{10}$ and $R_{11}$ are identical and are cyclohexyl, phenyl, t-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl.

13. A compound of the formula I according to claim 1, wherein $R_1$ is methyl and $R_2$ and $R_3$ are each cyclohexyl or phenyl and $R_{10}$ and $R_{11}$ are phenyl, cyclohexyl or t-butyl.

14. A compound of the formula I according to claim 1, wherein $R_{12}$ is $C_1$–$C_4$alkyl.

15. A compound of the formula I according to claim 1, wherein $R_{13}$ is $C_3$–$C_6$alkylene.

16. A compound of the formula I according to claim 1, wherein $R_{14}$ is $C_1$–$C_6$alkylene.

17. A compound of the formula I according to claim 1, wherein $R_{15}$ is $C_1$–$C_4$alkyl.

18. A compound of the formula I according to claim 1, wherein $R_a$ is $OR_{15}$.

19. A process for preparing compounds of the formula I according to claim 1, wherein, in a first step, a) compounds of the formula III

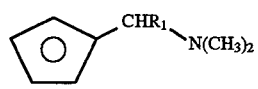 (III)

are reacted with butyllithium in an inert organic solvent in the presence of an amine complexing agent for lithium, the reaction product is subsequently reacted with a mixture of the compounds of the formulae IV $ClPR_{10}R_{11}$ (IV) and V $ClSi(R_{12})_2$-$(R_{13})$-Cl (V) to give compounds of the formula VI

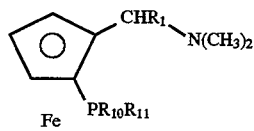 (VI)

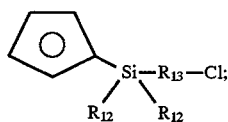

in a second step, b) Compounds of the formula VI are reacted in an organic solvent with compounds of the formula VII $HPR_2R_3$ (VII) to give compounds of the formula Ia

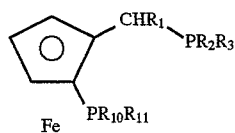

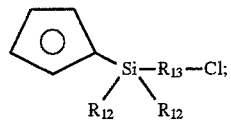

c) Compounds of the formula Ia are reacted with compounds of the formula VIII $NH_2(C_1-C_{12}alkyl)$ (VIII) to give compounds of the formula Ib

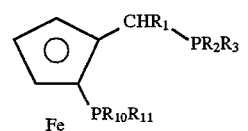

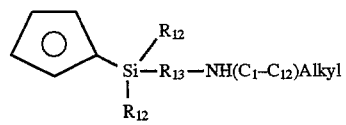

or compounds of the formula Ia are reacted first with potassium phthalimide and subsequently with hydrazine to give compounds of the formula Ic

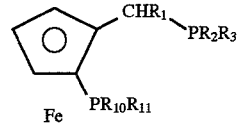

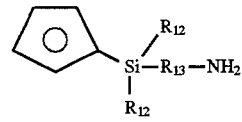

and, if desired in a further step, d) Compounds of the formula Ib or Ic are reacted with a compound of the formula IX $(R_a)_n(R_{15}O)_{3-n}Si-R_{14}-NCO$ (IX) to give compounds of the formula Id

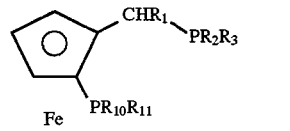

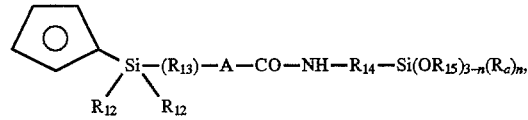

in which the radicals $R_a$, $R_1$, $R_2$, $R_3$, $R_{10}$, $R_{11}$, $R_{12}$, $R_{13}$, $R_{14}$, $R_{15}$, A and n are as defined in claim 1.

20. A metal complex of the formula Xa or Xb of a compound of the formula I

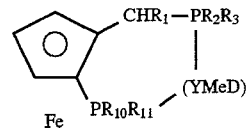

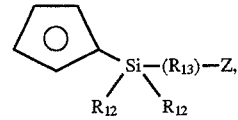

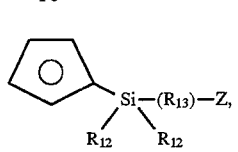

in which $R_1$, $R_2$, $R_3$, $R_{10}$, $R_{11}$, $R_{12}$, $R_{13}$ and Z are as defined in claim 1;

Y is two monoolefin ligands or a diene ligand;

Me is Ir or Rh;

D is —Cl, —Br, —I;

$E^-$ is the anion of an oxygen acid or a complex acid.

21. A process for preparing metal complexes of the formula Xa or Xb according to claim 20, wherein compounds of the formula I are reacted with a metal compound of the formula $[Me(Y)D]_2$ or $Me(Y)_2^+E^-$, in which Me is rhodium or iridium and Y, D and $E^-$ are as defined in claim 20.

22. An inorganic or polymeric organic support material to which ferrocenyldiphosphines are bound, wherein the 1 and 2 positions of the one cyclopentadienyl ring bears tertiary phosphine groups of which one is bound directly and the other via a group $CHR_1$ to the cyclopentadienyl ring and the other cyclopentadienyl ring bears a silylene group —$Si(R_{12})_2$-$R_{13}$-A- which is bound via the Si atom and forms one end of an organic bridge at the other end of which the inorganic or polymeric organic support is bound via the group A directly or via an additional bridging group, where the radicals A, $R_{12}$ and $R_{13}$ are as defined in claim 1.

23. A polymeric organic support material according to claim 22, having structural repeating units of the formula XI

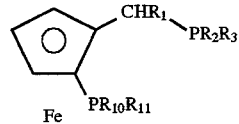

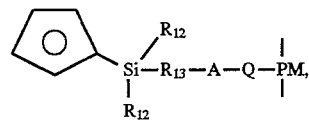

in which

A is NH or $N(C_1-C_{12}alkyl)$, $R_1$ is $C_1-C_8$alkyl, phenyl or phenyl substituted by from 1 to 3 $C_1-C_4$alkyl or $C_1-C_4$alkoxy groups;

$R_2$, $R_3$, $R_{10}$ and $R_{11}$, are independently of one another, $C_1-C_{12}$alkyl, $C_5-C_{12}$cycloalkyl, phenyl, $C_5-C_{12}$cycloalkyl substituted by $C_1-C_4$alkyl or $C_1$–$C_4$alkoxy, or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —($^+NR_7R_8R_9$) $X^-$ or $C_1$–$C_5$fluoroalkyl groups; or the groups —$PR_2R_3$ and —$PR_2R_3$ are each, independently of one another, a radical of the formula II, IIa, IIb or IIc

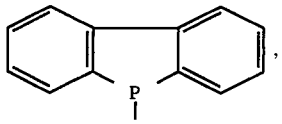   (II)

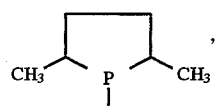   (IIa)

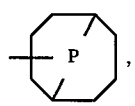   (IIb)

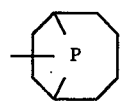   (IIc)

and $R_4$, $R_5$ and $R_6$ are, independently of one another, $C_1$–$C_{12}$alkyl or phenyl;

$R_7$ and $R_8$ are H, $C_1$–$C_{12}$alkyl, phenyl or $R_7$ and $R_8$ are together tetramethylene, pentamethylene or 3-oxa-1,5-pentylene, $R_9$ is H or $C_1$–$C_4$alkyl;

$R_{12}$ are identical or different radicals and are, independently of one another, $C_1$–$C_{12}$alkyl, $C_3$–$C_7$cycloalkyl, benzyl or phenyl or together are $C_5$–$C_{12}$alkylene and $R_{13}$ is $C_1$–$C_{12}$alkylene or phenylene, M is H or an alkali metal, $X^-$ is the anion of a monobasic acid, Q is a bridging group formed by a diisocyanate;

PM is the radical of a polymer-forming monomer which bears, directly or in a side chain, a hydroxyl group or a primary or secondary amino group as functional group which is bound to the diphosphine via the bridging group Q.

24. A process for preparing the polymeric support material according to claim 22, wherein the polymers containing structural repeating units of at least one monomer containing a bonded hydroxyl group or a bonded primary or secondary amino group as functional group directly in the polymer backbone or in a side chain A) are, in a first step, completely or partially reacted with a diisocyanate forming a bridging group Q in an inert organic solvent and the product is, in a second step, reacted with a diphosphine in which the 1 and 2 positions of one cyclopentadienyl radical bear tertiary phosphine groups of which one is bound directly and the other via a group $CHR_1$ to the cyclopentadienyl ring and the other cylcopentadienyl radical bears a silylene group —$Si(R_{12})_2$-$R_{13}$-A-;

or

B) in a first step, a diphosphine in which the 1 and 2 positions of one cyclopentadienyl radical bear tertiary phosphine groups of which one is bound directly and the other via a group $CHR_1$ to the cyclopentadienyl ring and the other cyclopentadienyl radical bears a silylene group —$Si(R_{12})_2$-$R_{13}$-A- is reacted with a diisocyanate forming a bridging group Q in an inert organic solvent and the product is, in a second step, completely or partially reacted with a polymer containing structural repeating units of at least one monomer containing a bonded hydroxyl group or a bonded primary or secondary amino group as functional group, where the radicals A, $R_{12}$ and $R_{13}$ are as defined in claim 1; and C) any free isocyanate groups still present are crosslinked with a $C_2$–$C_{24}$diol or $C_2$–$C_{24}$diamine or are reacted with a $C_2$–$C_{12}$alcohol or $C_2$–$C_{12}$amine.

25. A solid inorganic support material according to claim 22 having ferrocenyldiphosphine ligands of the formula XIII bound to its surface

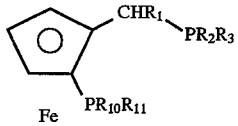   (XIII)

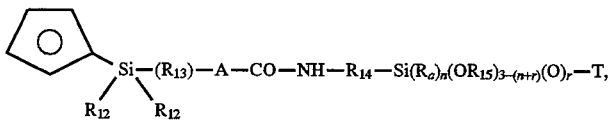

in which $R_1$ is $C_1$–$C_8$alkyl, phenyl or phenyl substituted by from 1 to 3 $C_1$–$C_4$alkyl or $C_1$–$C_4$alkoxy groups;

$R_2$, $R_3$, $R_{10}$ and $R_{11}$, are independently of one another, $C_5$–$C_{12}$alkyl, $C_5$–$C_{12}$cycloalkyl, phenyl, $C_5$–$C_{12}$cycloalkyl substituted by $C_1$–$C_4$alkyl or $C_1$–$C_4$alkoxy, or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —($^+NR_7R_8R_9$) $X^-$ or $C_1$–$C_5$fluoroalkyl groups; or the groups —$PR_2R_3$ and —$PR_{10}R_{11}$ are each, independently of one another, a radical of the formula II, IIa, IIb or IIc

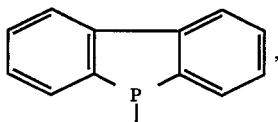   (II)

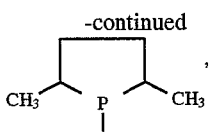 (IIa)

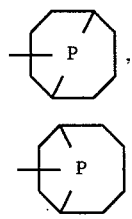 (IIb)

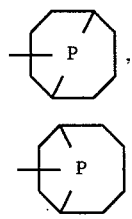 (IIc)

and $R_4$, $R_5$ and $R_6$ are, independently of one another, $C_1$–$C_{12}$alkyl or phenyl;

$R_7$ and $R_8$ are H, $C_1$–$C_{12}$alkyl, phenyl or $R_7$ and $R_8$ are together tetramethylene, pentamethylene or 3-oxa-1,5-pentylene, $R_9$ is H or $C_1$–$C_4$alkyl;

$R_{12}$ are identical or different radicals and are, independently of one another, $C_1$–$C_{12}$alkyl, $C_3$–$C_7$cycloalkyl, benzyl or phenyl or together are $C_5$–$C_{12}$alkylene and $R_{13}$ is $C_1$–$C_{12}$alkylene or phenylene, M is H or an alkali metal, $X^-$ is the anion of a monobasic acid, A is NH or N($C_1$–$C_{12}$alkyl), $R_{14}$ is $C_1$–$C_{12}$alkylene, $R_{15}$ is $C_1$–$C_{12}$alkyl, $R_a$ is $C_1$–$C_4$alkyl or $OR_5$, and T is a solid inorganic support material where r is 1, 2 or 3 when n is 0, r is 1 or 2 when n is 1 and r is 1 when n is 2.

26. A process for the assymetric hydrogenation of a compound containing a carbon-carbon or carbon-heteroatom double bond, wherein said compound is reacted at a temperature of from −20° to 80° C. and a hydrogen pressure of from $10^5$ to $2 \times 10^7$ Pa in the presence of a catalytic amount of one or more metal complexes of the formulae XIIa, XIIb, XIIIa or XIIIb

 (XIIa)

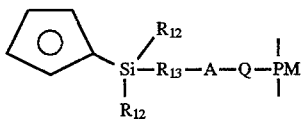

 (XIIb)

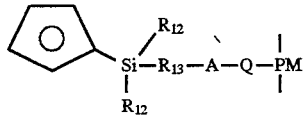

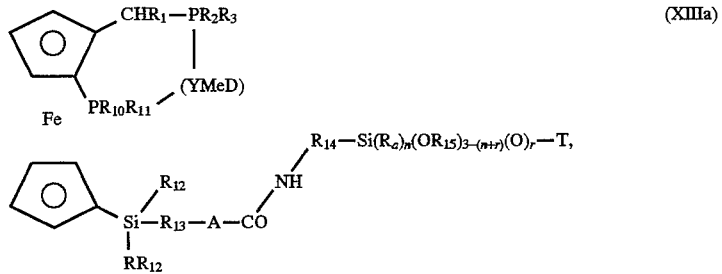 (XIIIa)

-continued

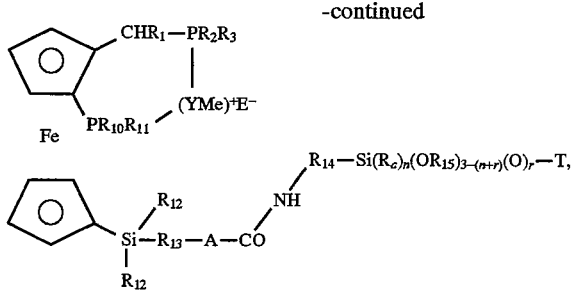

(XIIIb)

in which

R₁ is $C_1$–$C_8$alkyl, phenyl or phenyl substituted by from 1 to 3 $C_1$–$C_4$alkyl or $C_1$–$C_4$alkoxy groups;

R₂, R₃, R₁₀ and R₁₁, are independently of one another, $C_1$–$C_{12}$alkyl, $C_5$–$C_{12}$cycloalkyl, phenyl, $C_5$–$C_{12}$cycloalkyl substituted by $C_1$–$C_4$alkyl or $C_1$–$C_4$alkoxy, or phenyl substituted by from one to three $C_1$–$C_4$alkyl, $C_1$–$C_4$alkoxy, —SiR₄R₅R₆, halogen, —SO₃M, —CO₂M, —PO₃M, —NR₇R₈, –(⁺NR₇R₈R₉) X⁻ or $C_1$–$C_5$fluoroalkyl groups; or the groups —PR₂R₃ and —PR₁₀R₁₁ are each, independently of one another, a radical of the formula II, IIa, IIb or IIc

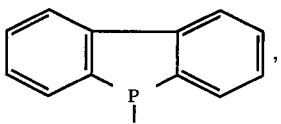 (II)

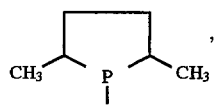 (IIa)

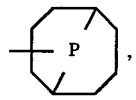 (IIb)

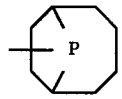 (IIc)

and

R₄, R₅ and R₆ are, independently of one another, $C_1$–$C_{12}$alkyl or phenyl;

R₇ and R₈ are H, $C_1$–$C_{12}$alkyl, phenyl or

R₇ and R₈ are together tetramethylene, pentamethylene or 3-oxa-1,5-pentylene,

R₉ is H or $C_1$–$C_4$alkyl;

R₁₂ are identical or different radicals and are, independently of one another, $C_1$–$C_{12}$alkyl, $C_3$–$C_7$cycloalkyl, benzyl or phenyl or together are $C_5$–$C_{12}$alkylene and R₁₃ is $C_1$–$C_{12}$alkylene or phenylene, M is H or an alkali metal, X⁻ is the anion of a monobasic acid, A is NH or N($C_1$–$C_{12}$alkyl), R₁₄ is $C_1$–$C_{12}$alkylene, R₁₅ is $C_1$–$C_{12}$alkyl, $R_a$ is $C_1$–$C_4$alkyl or OR₁₅, n is 0, 1 or 2, Y is two monoolefin ligands or a diene ligand;

Me is Ir or Rh;

D is —Cl,—Br, —I;

E⁻ is the anion of an oxygen acid or a complex acid,

Q is a bridging group formed by a diisocyanate;

PM is the radical of a polymer-forming monomer which bears, directly or in a side chain, a hydroxyl group or a primary or secondary amino group as functional group which is bound to the diphosphine via the bridging group Q formed by the diisocyanate, and T is a solid inorganic support material where r is 1, 2 or 3 when n is 0, r is 1 or 2 when n is 1 and r is 1 when n is 2.

* * * * *